(12) United States Patent
Espina et al.

(10) Patent No.: US 8,460,859 B2
(45) Date of Patent: Jun. 11, 2013

(54) TISSUE PRESERVATION AND FIXATION METHOD

(75) Inventors: Virginia A. Espina, Rockville, MD (US); Lance A. Liotta, Bethesda, MD (US); David Geho, Oakton, VA (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 545 days.

(21) Appl. No.: 12/447,773

(22) PCT Filed: Oct. 26, 2007

(86) PCT No.: PCT/US2007/022744
§ 371 (c)(1),
(2), (4) Date: Apr. 29, 2009

(87) PCT Pub. No.: WO2008/073187
PCT Pub. Date: Jun. 19, 2008

(65) Prior Publication Data
US 2010/0068690 A1    Mar. 18, 2010

Related U.S. Application Data

(60) Provisional application No. 60/855,120, filed on Oct. 30, 2006, provisional application No. 60/861,086, filed on Nov. 27, 2006.

(51) Int. Cl.
*A01N 1/00* (2006.01)
(52) U.S. Cl.
USPC .......................................................... 435/1.1
(58) Field of Classification Search
None
See application file for complete search history.

(56) References Cited

U.S. PATENT DOCUMENTS

| | | |
|---|---|---|
| 5,679,333 A | 10/1997 | Dunphy |
| 2006/0099567 A1 | 5/2006 | Muller-Cohn et al. |
| 2009/0017437 A1 | 1/2009 | Boon |

FOREIGN PATENT DOCUMENTS

| | | |
|---|---|---|
| WO | WO2004/033622 A3 | 4/2004 |
| WO | WO 2005/113147 | * 12/2005 |
| WO | WO2008/073187 A3 | 7/2009 |

OTHER PUBLICATIONS

Nayler et al., "The Cellular Localization of the Murine Serine/Arginine-rich Protein Kinase CLK2 Is Regulated by Serine 141 Autophosphorylation", The Journal of Biological Chemistry, 1998, 273(51):34341-34348.*
Written Opinion of the International Searching Authority of WIPO on International App. No. PCT/US2007/022744 (WO 08/073187) of George Mason Intellectual Properties, Inc., Apr. 11, 2009.
International Preliminary Report on Patentability of the International Bureau of WIPO on International App. No. PCT/US2007/022744 (WO 08/073187) of George Mason Intellectual Properties, Inc., Nov. 26, 2009.
European Patent Office Communication Pursuant to Article 94(3) EPC for App. No. 07 870 821.1-2103 of George Mason Intellectual Properties, Inc., Feb. 14, 2012.
Examination Report of the Intellectual Property Office of New Zealand on App. No. 576794 of George Mason Intellectual Properties, Inc., Jul. 6, 2010.
Bodo et al., "Quantitative in Situ Detection of Phosphoproteins in Fixed Tissues Using Quantum Dot Technology," vol. 57(7), pp. 701-708, 2009 (J. Histochemistry & Cytochemistry).

* cited by examiner

*Primary Examiner* — Suzanne M Noakes
(74) *Attorney, Agent, or Firm* — Geoffrey M. Karny

(57) ABSTRACT

This invention relates, e.g., to a composition that, at room temperature, when contacted with a sample comprising phosphoproteins, can fix and stabilize cellular phosphoproteins, preserve cellular morphology, and allow the sample to be frozen to generate a cryostat frozen section suitable for molecular analysis. The composition comprises (1) a fixative that is effective to fix the phosphoproteins, and that has a sufficient water content to be soluble for a stabilizer and/or a permeability enhancing agent); (2) a stabilizer, comprising (a) a kinase inhibitor and (b) a phosphatase inhibitor and, optionally, (c) a protease (e.g., proteinase) inhibitor; and (3) a permeability enhancing agent (e.g. PEG). Methods are described for preserving phosphoproteins, using such a composition. Also described are endogenous surrogate markers for monitoring protein degradation, including the loss of post-translational modifications (such as phosphorylation), e.g. the following removal of a cell or tissue from a subject; and exogenous molecular sentinels (e.g. phosphoproteins attached to magnetic nanoparticles) that allow one to evaluate the processing history of a cellular or tissue population sample.

29 Claims, 19 Drawing Sheets

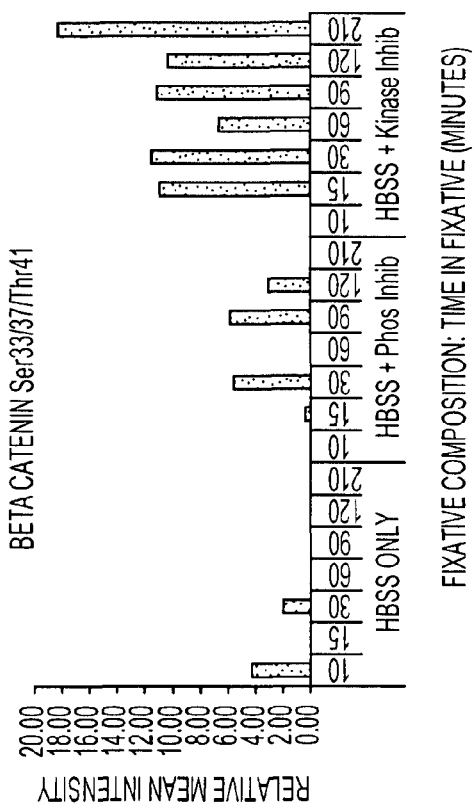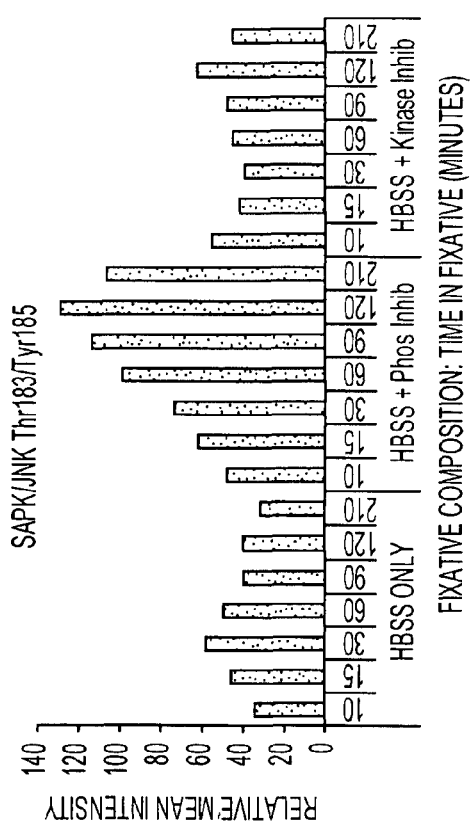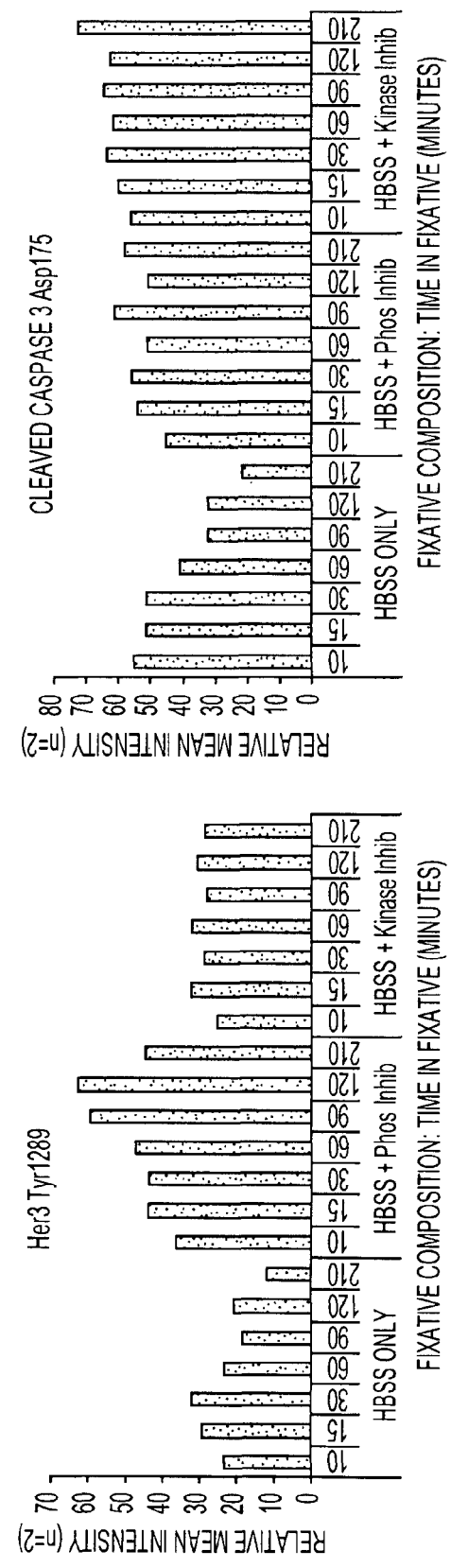

TISSUE PRESERVATION AND FIXATION METHOD

This application claims the benefit of the filing date of U.S. Provisional Application No. 60/855,120, filed Oct. 30, 2006, and U.S. Provisional Application No. 60/861,086, filed Nov. 27, 2006, both of which are incorporated by reference herein in their entirety.

This invention was made with government support under the following grants awarded by the National Institutes of Health: 1R21CA155592-01, 1R33CA157403-01, 3R21CA125698-02S1, 1R21CA125698-01, 3R21CA125698-02S2, 5R21CA125698-02, and 5R33CA157403-03. The government has certain rights in the invention.

BACKGROUND INFORMATION

Phosphoprotein molecular profiling is an important component of the emerging field of individualized cancer therapy. Molecularly targeted anti-cancer therapeutics often involves the mitigation or modulation of defective kinase signaling networks. Elucidation of deranged signaling networks within tumors offers tremendous promise as a means to individualize molecular targeted cancer therapy and to identify entirely new targets for therapeutic intervention. Evidence from molecular signature/transcript studies using gene microarrays (nucleic acid analysis) suggests that each patient's tumor may have a unique genetic portrait. Nevertheless, while gene microarrays can provide important information about somatic genetic taxonomy, they are unable to provide an effective recapitulation of the drug targets themselves, which are embodied in the post-translational and fluctuating signaling molecular network events that occur at the proteomic level. The phosphorylation, or activation state, of kinase-driven signal networks contains important information concerning both disease pathogenesis and the ongoing state of kinase-associated therapeutic targets. It is for this reason that modulation of ongoing cellular kinase activity represents one of the most rapidly growing arenas in new drug discovery. Identification of specific phosphoprotein signaling aberrations can be used, e.g., for the development of targeted therapies for patients with lung, breast, colon, or other cancer. Profiling the tumor phosphoproteome using human tumor biopsy specimens is an important component of the perceived upcoming revolution of individualized cancer therapy.

While proteomic molecular profiling offers tremendous promise to change the practice of oncology, the fidelity of the data obtained from a diagnostic assay applied to tissue must be monitored and ensured; otherwise, a clinical decision may be based on incorrect molecular data. To date, clinical preservation practices routinely rely on protocols that are decades old, such as formalin fixation, and are designed to preserve specimens for histologic examination. Tissue is generally procured for pathologic examination in three main settings: a) surgery in a hospital-based operating room, b) biopsy conducted in an outpatient clinic, and c) image-directed needle biopsies or needle aspirates conducted in a radiologic suite. Currently, tissue is generally snap-frozen in order to perform proteomic studies. In the real world of a busy clinical setting, it may be impossible to immediately preserve procured tissue in liquid nitrogen. Moreover, the time delay from patient excision to pathologic examination and molecular analysis is often not recorded and may vary from 30 minutes to many hours depending on the time of day, the length of the procedure, and the number of concurrent cases.

FIG. 1 depicts the two categories of variable time periods that define the stability intervals for tissue procurement (e.g. from human tissue). Time point A is defined as the moment that tissue is excised from the patient and becomes available ex vivo for analysis and processing. The post excision delay time, or EDT, is the time from time point A to the time that the specimen is placed in a stabilized state, e.g., immersed in fixative or snap-frozen in liquid nitrogen, herein called time point B. Given the complexity of patient-care settings, during the EDT the tissue may reside at room temperature in the operating room or on the pathologist's cutting board, or it may be refrigerated in a specimen container. The second variable time period is the processing delay time, or PDT. At the beginning of this interval the tissue is immersed in a preservative composition or stored in a freezer. At the end of this interval, time point C, the tissue is subject to processing for molecular analysis. In addition to the uncertainty about the length of these two time intervals, a host of known and unknown variables can influence the stability of tissue molecules during these time periods. These include 1) temperature fluctuations prior to fixation or freezing, 2) preservative chemistry and rate of tissue penetration, 3) size of the tissue specimen, 4) extent of handling, cutting, and crushing of the tissue, 5) fixation and staining prior to microdissection, 6) tissue hydration and dehydration, and 7) the introduction of phosphatases or proteinases from the environment at any time.

There is a need for methods to collect and preserve (fix and stabilize) proteins, including post-translationally modified proteins, such as phosphoproteins (e.g. within about four hours of corporal extraction), and for methods to monitor the status (e.g. phosphorylation state) of proteins during the EDT and PDT periods.

DESCRIPTION OF THE DRAWINGS

FIG. 3 shows a post excision delay time study. One uterine resection was divided into 25 pieces. The pieces were allowed to incubate in an open Petri dish at 4° C. or room temperature. Over a course of 90 minutes, pieces were removed at abut 15 minute intervals and were analyzed for 10 different endpoints by Reverse Phase Protein Microarray (RPMA).

FIG. 4 shows chemical stabilizers applied to cellular samples for evaluation of phosphoprotein preservation. Fine Needle Aspirate (FNA) samples were stored for 24 hours at 4° C. in each of the chemicals/chemical solutions. The cellular samples were further processed for reverse phase protein microarray analysis.

FIG. 6 shows methanol: water fixative versus frozen tissue for phosphoprotein stability.

FIG. 8 shows the effect on phosphoprotein stabilization of adding to a base fixative either a phosphatase inhibitor or a kinase inhibitor. Samples were harvested and analyzed for the presence of selected phosphoprotein endpoints, at the times indicated in the figure. FIG. 8A shows the endpoint, SAPK/JNK (Thr183/Tyr185); FIG. 8B shows beta catenin (S33/37/Thr41); FIG. 8C shows the endpoint, Her3 (Tyr1289); FIG. 8D shows CC3 (Asp175).

FIG. 10 shows line graphs depicting the surge of phosphorylation seen over time in the presence of a phosphatase inhibitor (pervanadate) in an in vitro cell culture model (in living cells).

FIG. 11 depicts images (stained with Hematoxylin and Eosin) showing the morphology of uterine tissue fixed in various fixative formulations at room temperature.

FIG. 12 shows Laser capture microdissection of uterine tissue fixed with 10% ethanol+PEG+protease inhibitors.

FIGS. 13 A-D show FACS analysis of cells stained for CD4, which have been fixed and stabilized with a preservative composition of the invention.

DESCRIPTION OF THE INVENTION

The present invention provides, e.g., for methods for preserving and monitoring proteins in a sample obtained form a subject, particularly post-translationally modified proteins, including phosphoproteins. In one embodiment of the invention, the preserved proteins are phosphoproteins which represent the phosphoproteome repertoire of human tumor tissue obtained from clinical specimens. Aspects of the invention include compositions (e.g., solutions) for sample preservation (fixation and stabilization) at room temperature; the identification of surrogate endogenous markers that can be used for quality control monitoring of samples, e.g. samples that have been removed from a subject but not yet subjected to a stabilization procedure; and sentinels (e.g. panels of sentinels) comprising exogenous markers that can be used for quality assessment, e.g. monitoring of a sample between the time a sample has been subjected to a stabilization procedure and the time that a further procedure (e.g. molecular analysis) is carried out.

Particular preservation requirements exist for procured tissue samples, especially within the first 3-4 hours following corporal extraction. The present inventors show herein that, unexpectedly, an excised (procured) tissue from a subject can continue to live and to react to the absence of vascular perfusion, ischemia, hypoxia, acidosis, accumulation of cellular waste, absence of electrolytes, temperature changes, etc. for several hours, between the time the tissue is excised (procured) and the time at which it is exposed to a preservative. The inventors show that, in spite of being removed from their microenvironments and sources of energy, signaling ligands, and oxygen source, the phosphoproteins in the excised sample continue to undergo metabolic changes—both activation and deactivation of phosphoproteins—through the action of endogenous kinases and phosphatases, respectively.

Figure 10A:
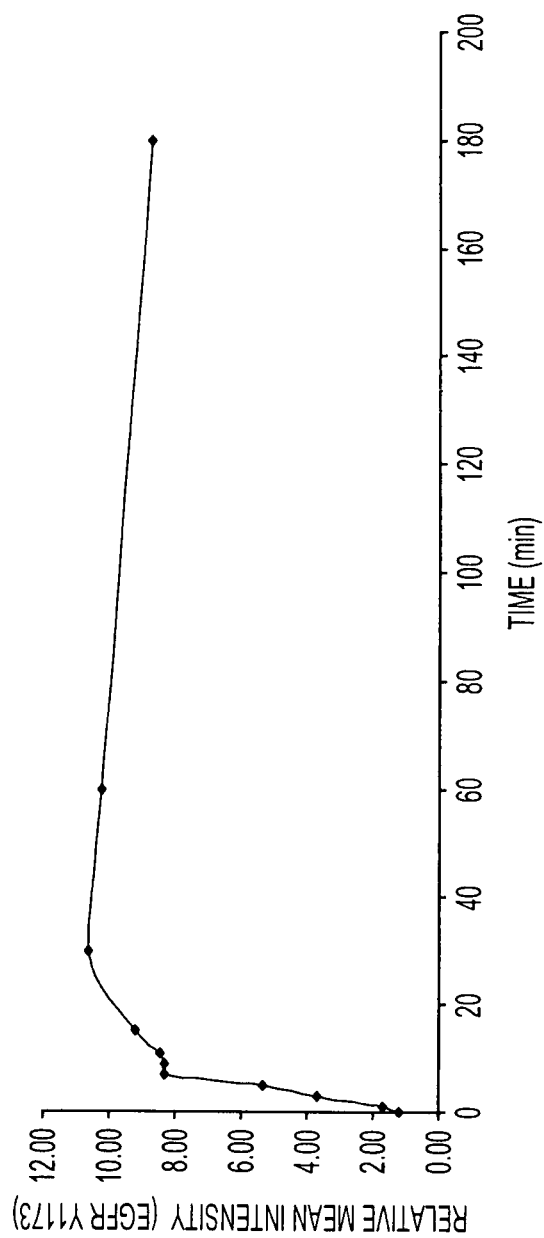
FIG. 10A shows the effect of the phosphatase inhibitor on the phosphorylation of EGF receptor (EGFR Y1173). The phosphorylation rises rapidly to a high level in less than 40 minutes, which is followed by cell death.
Figure 10B:
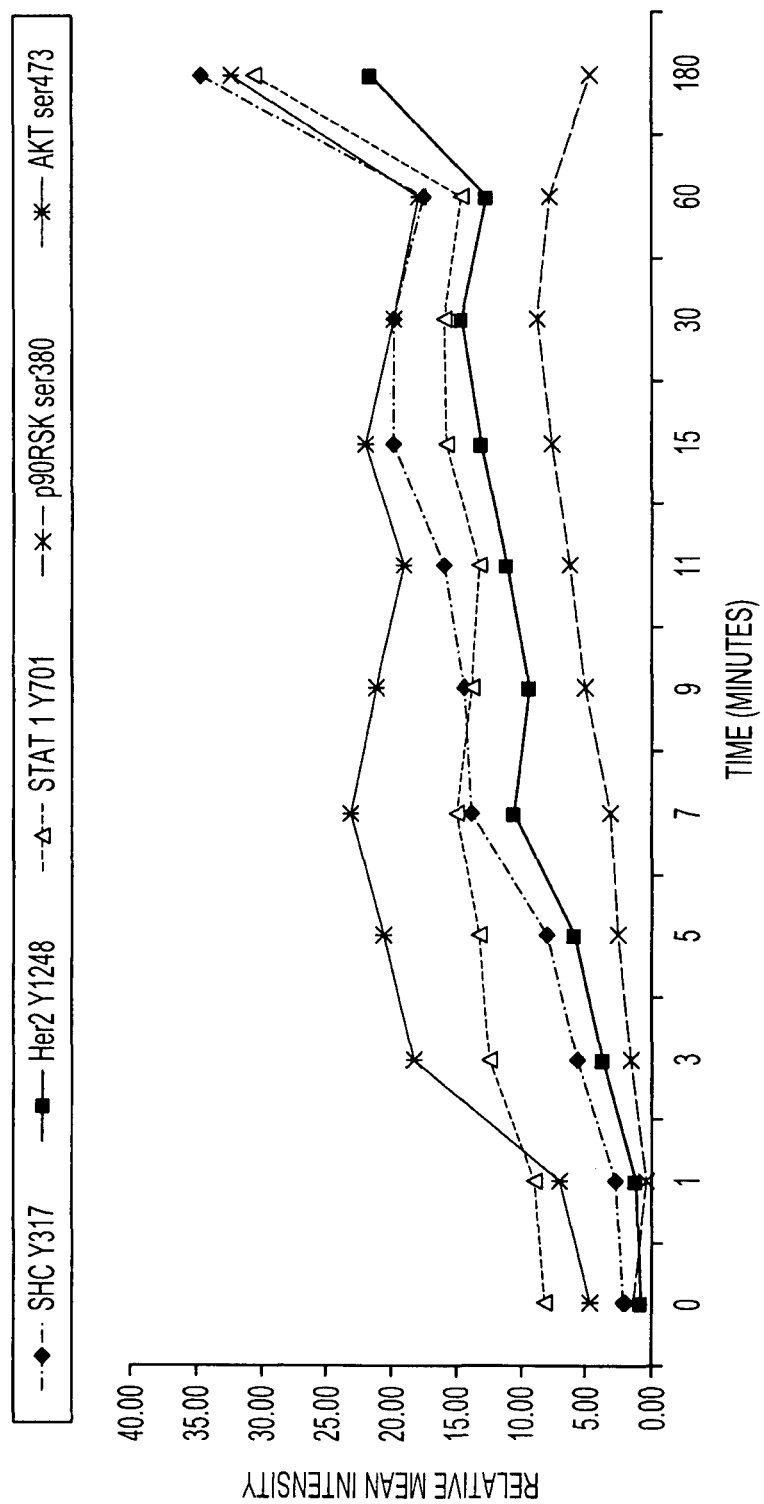
FIG. 10B shows hyperphosphorylation over time for a series of listed phospho-endpoints, following exposure of the living cells to the phosphatase inhibitor.
Figure 11A:
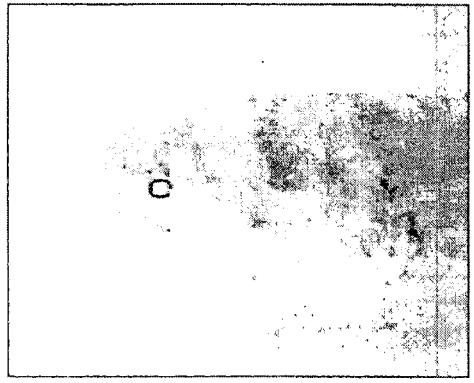
FIG. 11A: 10% methanol 2× magnification.
Figure 11B:
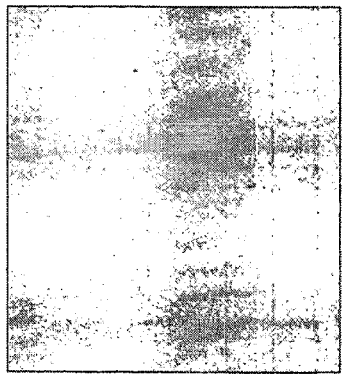
FIG. 11B: Frozen tissue embedded in Optimal Cutting Compound 2× magnification.
Figure 11C:
FIG. 11C: Formalin 10× magnification.
Figure 11D:
FIG. 11D: 10% Methanol 10× magnification.
Figure 11E:
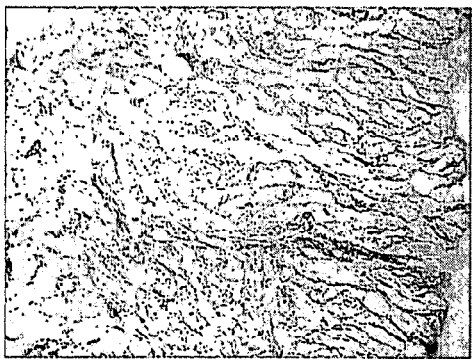
FIG. 11E: 10% Methanol+ Polyethylene glycol 10× magnification.
Figure 11F:
FIG. 11F: 10% Methanol+PEG+protease and phosphatase inhibitors 10× magnification.

These continuing metabolic processes present problems for the preservation of phosphoproteins in a sample. For example, the inventors have discovered that the addition of a phosphatase inhibitor alone, designed to block the removal of protein phosphate groups by endogenous phosphatases, can cause unchecked and highly abnormal upward accumulation of abnormal levels of phosphoproteins, reaching a lethal level. See, e.g., FIG. 10, which shows a large surge of phosphorylation following the treatment of a cultured cell line (A549) with the tyrosine phosphatase inhibitor, pervanadate. Without wishing to be bound by any particular mechanism, it is suggested that this surge occurs because, while the phosphatase inhibitor prevents de-phosphorylation of kinases, the kinases, themselves, remain active and continue to phosphorylate proteins.

Thus, in order to achieve an accurate reflection of the molecules (e.g. phosphoproteins) in living tissue at the time of excision, it is important to fix tissue as soon as possible after procurement, and to arrest reactive fluctuations in the cellular signaling and metabolic functions until the time of assay.

The inventors identify herein a composition (a preservative composition) that, when contacted with a sample comprising phosphoproteins at room temperature, can fix and stabilize the phosphorylation state of the phosphoproteins (e.g., inhibit phosphatases, kinases and, optionally, proteases), in a single step, under conditions which preserve cellular morphology and tissue histology, and which do not impede freezing of the sample for further processing (e.g. preparing frozen sections or long-term cryogenic storage).

A first component of a preservative composition of the invention is a fixative (e.g. a solution) which is able to precipitate and thus fix proteins within cells, yet which contains a sufficient water content so that stabilizers, such as inhibitors of phosphatases, kinases and/or proteases, are soluble and can enter and function within the fixed cell.

In view of the observations herein that both activation and deactivation of phosphoproteins continue to occur in cells or tissues after they have been procured, a preservative composition of the invention further comprises, as a second component, a stabilizer, which comprises at least one kinase inhibitor and at least one phosphatase inhibitor and, optionally, at least one protease inhibitor.

A third component that is generally present in a preservative composition of the invention is a permeability (permeation) enhancing agent (reagent), which can enhance the rapid penetration of the fixative and/or stabilizer from the surface of a cell or tissue into the inner mass of a cell or tissue. The permeability enhancer can be, e.g., polyethylene glycol (PEG). (In some embodiments of the invention, when it is not necessary to fix and stabilize components that are inside a cell, the permeability enhancing reagent may not be required. For example, when preserving cells for FACS sorting, for which it is only important for antigenic surface proteins on the surface of a cell to be fixed and stabilized, it may not be necessary to include a permeability enhancing agent.)

A composition that comprises a fixative, a stabilizer, and a permeability enhancing agent, is sometimes referred to herein as a "composition of the invention" or a "preservative composition of the invention."

A composition of the invention, when contacted with a cell or tissue, will generate a rapidly moving solvent front that quickly penetrates through the tissue volume, arrests fluctuations (both increases and decreases) in signal pathways within the living cells reacting to the shock of excision, while simultaneously fixing, arresting, and/or precipitating the cellular molecules and preserving the cellular morphology for histopathology diagnosis following frozen section or paraffin sectioning. The stabilizer component of the composition can, e.g., inhibit signal pathway activation occurring in living tissue cells prior to full fixation or the arrest of cellular molecules by the fixative moving front. All of these functions are accomplished at room temperature.

The inventors identify herein phosphoproteins that, unexpectedly, are particularly labile (exhibit changes in phosphorylation state) in samples that have been removed from a subject. These phosphoproteins (as well as other proteins discussed herein) can serve as endogenous surrogate markers, which can be used for measuring the state of phosphoprotein preservation in a sample (e.g., from a cell, tissue, bodily fluid or product of a cell). Such analysis can be used to determine if other proteins in a given sample are sufficiently well-preserved for the sample to be suitable for further analysis, e.g. proteomic analysis. The identified labile phosphoproteins, or other proteins, can also be attached to (e.g. bound to, coupled to, immobilized on) particulate matter to form exogenous sentinels, which can be used, for example, to evaluate the processing history of a cellular or tissue population sample. If desired, panels of a variety of such exogenous sentinel molecules can be used.

Advantages of methods of the invention include that, because the preservation is conducted at room temperature, the need for expensive refrigeration is eliminated. Methods of the invention facilitate the analysis of samples in a clinical environment, and under conditions (e.g. in impoverished settings or in a battlefield) in which refrigeration is not available. Methods of the invention allow for the rapid, accurate and reproducible preparation of samples for further analysis, such as molecular diagnostic analysis based on the phosphorylation state of selected phosphoproteins. Cellular and histologic morphology is preserved for pathologic diagnosis. Moreover, in methods of the invention, fixative and stabilization agents can rapidly penetrate from the surface of an immersed or treated tissue into the inner mass of the tissue. Because of the rapid introduction of a fixative into a cell or tissue, methods of the invention overcome the problems of conventional fixatives, such as formalin, which penetrates slowly (millimeters per hour) and aldehyde, whose cross-linking lags behind many hours, during which time the tissue to be preserved may still be undergoing metabolic reactions.

The invention relates, e.g., to a composition (a preservative composition) that, at room temperature, when contacted with a sample comprising phosphoproteins, can fix and stabilize the phosphoproteins, preserve cellular morphology, and allow the sample to be frozen to generate a cryostat frozen section suitable for molecular analysis, wherein the composition comprises (1) a fixative that is effective to fix the phosphoproteins, and that has a sufficient water content to be soluble for a stabilizer and/or a permeability enhancing agent;

(2) a stabilizer, comprising (a) a kinase inhibitor and (b) a phosphatase inhibitor and, optionally, (c) a protease (e.g. proteinase) inhibitor; and (3) a permeability enhancing agent.

As used herein, the singular forms "a," "an" and "the" include plural referents unless the context clearly dictates otherwise. For example, "a" kinase inhibitor, as used above, includes one or more such inhibitors.

Another aspect of the invention is a method for preserving (fixing and stabilizing) one or more phosphoproteins in a sample that comprises a cell, a tissue, a bodily fluid, or a product of a cell, at room temperature, comprising contacting the sample at room temperature with a composition of the invention, under conditions effective for the preservation of phosphoproteins in the sample. The method may further comprise freezing the preserved sample (e.g., when the sample comprises a tissue) and, optionally sectioning the frozen, preserved sample. In one embodiment, the preservation method provides a matrix for freezing and sectioning of a tissue without the requirement for paraffin embedding. In a preservation method of the invention, one may further analyze the phosphoprotein state of at least one phosphoprotein in at least a subset of the cells in the sample. If desired, one can denature the phosphoproteins by treatment with an external source of energy (e.g. ultrasound, infrared, microwave, electromagnetic, RF (radio frequency) energy, or pressure, thermal, or chemical) before they are preserved.

"Effective conditions" for preserving phosphoproteins in a sample are a function of a number of variables, including the nature of the components of the preservative composition that is used, the nature of the sample, or the like. Suitable conditions can be routinely optimized by a skilled practitioner.

Another aspect of the invention is a method for determining the preservation state phosphoproteins in a sample (e.g. a sample which comprises a cell, a tissue, a bodily fluid, or a product of a cell). The method may allow an investigator to determine if the proteins in the sample are sufficiently stabilized to perform a subsequent (accurate, meaningful) molecular proteomic analysis of the sample. The method comprises determining if certain particularly labile (relatively labile) proteins in the sample are stabilized. By "sufficiently stabilized" is meant stabilization of positive or negative fluctuations of the level of post-translationally modified (e.g. phosphorylated) forms of the proteins such that the fluctuations ex vivo over time are no more than 20% of the baseline value existing at the instant immediately prior to when the tissue was immersed in the stabilizing treatment.

These endogenous markers are sometimes referred to herein as "endogenous surrogate markers" or "endogenous surrogate phosphoproteins." The endogenous surrogate markers may be, e.g., one or more of the phosphoproteins listed in Table 1. In a method to determine the preservation state of phosphoproteins, the sample may have been removed from a subject, but not yet subjected to a stabilization procedure (e.g. it may have been removed fewer than four hours preceding the stabilization procedure). A method to determine the preservation state may further comprise deciding, on the basis of the determined preservation state of the phosphoproteins, whether to proceed with molecular diagnostic analysis.

Another aspect of the invention is a set of antibodies specific for the phosphorylated isoforms and/or of the non-phosphorylated isoforms of one or more of the endogenous surrogate markers of the invention, e.g., one or more of the phosphoproteins listed in Table 1; at least about 5 of those phosphoproteins; at least about 10 of those phosphoproteins; or the particularly labile phosphoproteins in that table, STAT-3 or STAT-1 (e.g., STAT-3), CC-3 (cleaved caspase-3) and ASK-1. Other antibodies that may also be present in the set of antibodies include antibodies specific for one or more of the proteins listed in Table 2; for p-selectin, e-selectin, IL-2, IL-6, IL-8 and/or fibronectin; and/or for any of the other endogenous surrogate markers discussed herein. The antibodies may be, e.g., polyclonal or monoclonal. In fact, any ligand which is specific for one of the endogenous, surrogate proteins, and which can be used in a method to determine the preservation state of phosphoproteins in a sample, can be used and can be present in the kit.

Another aspect of the invention is a method for determining the preservation state of phosphoproteins in a sample (e.g., a sample which comprises a cell, a tissue, a bodily fluid, or a product of a cell) at two different time points, comprising contacting the sample with a sentinel comprising a (one or more) surrogate phosphoprotein marker at the first time point (under conditions effective for introducing the sentinel into cells in the sample), removing the sentinel at the second time point, and measuring and comparing the phosphorylation state of the surrogate phosphoprotein marker(s) associated with the sentinel at the two time points. The sentinel may be introduced into the sample at substantially the same time the sample is placed into a preservative composition of the invention. The sentinel(s) may be present in the receptacle with preservative composition into which the sample is introduced, or it may be added to the sample/preservative composition substantially immediately after the sample has been placed therein.

A "sentinel," as used herein, refers to an exogenous particulate entity that is associated with one or more phosphoproteins (e.g. highly labile phosphoproteins). Properties of sentinels of the invention are discussed in more detail elsewhere herein. The method can be used to monitor the stability of proteins in a sample. The method can be used to determine the amount of time between the removal of the sample from a subject and the start of a procedure (e.g., a fixation/preservation procedure).

Another aspect of the invention is a method for the molecular characterization (e.g. molecular diagnostic analysis) of one or more phosphoproteins of interest in a sample comprising a cell, tissue, bodily fluid, or product of a cell, when the sample is removed from a subject, comprising at a first time point, when the sample is taken from the subject, contacting the sample simultaneously, at room temperature, with a (one or more) sentinel of the invention and a preservative composition of the invention, thereby fixing and stabilizing the phosphoproteins of interest in the sample;

at a second time point, extracting the sentinel;

then measuring the preservation state of the surrogate phosphoprotein marker(s) associated with the sentinel, and, if the preservation state of the surrogate phosphoprotein marker(s) indicates that the preservation state of the phosphoprotein(s) of interest in the sample is adequate for its molecular characterization, performing molecular characterization of the phosphoprotein(s) of interest.

Another aspect of the invention is a kit for fixing and stabilizing phosphoproteins in a sample (e.g. a sample which comprises a cell, a tissue, a bodily fluid, or a product of a cell), at room temperature, comprising the components of a preservative composition of the invention, optionally in one or more containers. Another aspect of the invention is a kit for monitoring the preservation state of proteins (e.g., phosphoproteins) in a sample. The kit comprises one or more sentinels of the invention, in one or more containers, and optionally contains reagent for monitoring (measuring) the phosphorylation state of the proteins and/or instructions for use of the kit.

Another aspect of the invention is a device for collecting and preserving a cellular or tissue specimen, comprising a first chamber that excises or procures a specified volume of sample (e.g. a needle), connected to a second chamber that contains a preservative composition of the invention, such that with a single operation the sample is procured and immersed in the preservative in the chamber. The second chamber may be removable and used directly for further analysis, e.g. tissue sectioning or molecular processing.

A "sample," as used herein, can comprise any suitable cell, tissue, bodily fluid, or product of a cell (e.g. a protein) that can be fixed and preserved by a method of the invention (and, optionally assayed, e.g. to determine the phosphorylation state of one or more of the phosphoproteins in the sample). Suitable samples include, e.g., tissues, including surgical excisions or tissue biopsies, such as needle biopsies; cells that have been disaggregated from a cellular population by a suitable method, e.g. by mechanical means, or by aspirating a sample, such as a tumor sample, with a fine needle or other suitable device; bodily fluids, such as blood, vitreous humor, or a fraction of one or those fluids; or products of a cell, such as proteins that have been shed, secreted, excreted or otherwise obtained from the cell. A sample may be taken be from any subject (patient), e.g., any animal, including laboratory animals (such as mouse, rat, rabbit, or guinea pig), farm animals, domestic animals or pets (such as a cat or dog), non-human primates or, preferably, humans.

The "phosphorylation state" of a protein refers to the degree of (total amount of) phosphorylation of the protein. This includes both the number of sites (e.g. suitable Ser, Thr or Tyr amino acid residues) of the protein that are phosphorylated, and/or the level of phosphorylation at any given acceptor site on the amino acid chain. The "preservation state" of a sample reflects the condition of the sample and proteins etc. therein, including the phosphorylation state of the phosphoproteins.

The present inventors have identified fixatives (fixation agents) that not only precipitate and thus fix proteins in a sample, but also contain a sufficient amount of water so that stabilizers (stabilization agents, including proteins) remain soluble in the fixative. In general, the fixative contains a non-cross-linking precipitating agent in an aqueous base, such as, e.g., ethanol (e.g. about 10-40%, about 10-20%, or about 12%), methanol (e.g. about 10-40%, about 10-20%, or about 12%), benzyl alcohol (e.g. about 10-40%) or acetone (e.g. about 5-15%) (all V/V). As used herein, the term "about" means plus or minus 10%. For example, about 1% includes 0.9% to 1.1%. The endpoints of ranges, as used herein, are included within the range. For example, a range of 5-15% (e.g., a value of "between 5% and 15%") includes both 5% and 15%. The inventors have determined, unexpectedly, that the preceding low amounts of these precipitation fixatives are superior to conventional amounts of the alcohols (e.g. about 50-60%), for several reasons. Unlike the conventional levels, these low levels allow agents such as kinase and phosphatase inhibitors to stay in solution, and the low levels are particularly effective for the preservation of cellular morphology and preparing frozen sections.

Other types of suitable fixatives include solutions or suspensions of the following components, which are in a dilute enough form so that stabilizers and/or permeability reagents of the invention will be soluble: agents that can remove water or induce protein precipitation or aggregation, such as the particulate materials, bioceramic, poly diol citrates, chitosan, and hydroxyapatite (0.1-10% w/w); chelation agents (e.g., EDTA) (0.05%); trichloroacetic acid (TCA)(1-5%); chloroform/methanol (10-40%); or ammonium sulfate (5-15%).

A second component of a composition of the invention is a stabilizer (stabilizing agent) which comprises a kinase inhibitor (an inhibitor of signal pathway activation) and a phosphatase inhibitor (which inhibits the removal of a post-translational phosphorylation). Optionally, a stabilizer of the invention may also comprise a protease inhibitor.

Among the suitable kinase inhibitors that can be used are, e.g., Adaphostin; AG 490; AG 825; AG 957; AG 1024; Aloisine (e.g. Aloisine A); Alsterpaullone; Aminogenistein; API-2; Apigenin; Arctigenin; AY-22989; Bisindolylmaleimide IX; BMS-354825 (Dasatinib); Chelerythrine; DMPq; DRB; Edelfosone; Erbstatin analog; ET180CH3; ERK inhibitor fasudil; Gefitinib; H-7; H-8; H-89; HA-100; HA-1004; HA-1077; HA-1100; Hydroxyfausdil; Indirubin-3'-oxime; 5-Iodotubercidin; Kenpaullone; KN-62; KY12420; LFM-A13; Luteolin; LY-294002; Mallotoxin; M L-9; NSC-154020; NSC-226080; NSC-231634; NSC-664704; NSC-680410; NU6102; Olomoucine; Oxindole I; PD 153035; PD 98059; Phloridzin; Piceatannol; Picoropodophyllin; PKI; PP1; PP2; Purvalanol A; Quercetin; RAPA; Rapamune; Rapamycin; Ro 31-8220; Roscovitine; Rottlerin; SB202190; SB203580; Sirolimus; SL327; SP600125; Staurosporine; STI-571; SU1498; SU4312; Su6656; Syk inhibitor; TBB; TCN; Triciribine; Tyrophostin AG 490; Tyrophostin AG 825; Tyrophostin AG 957; Tyrophostin AG 1024; U0126; W-7; Wortmannin; Y-27632; ZD 1839; and ZM 252868. All of these agents, and other agents discussed herein, can readily be obtained from commercial sources, such as Sigma or Calbiochem.

Among the suitable phosphatase inhibitors that can be used are, e.g., A-Napthyl acid phosphatase; Calyculin A, Nodularin, NIPP-1 (inhibits PP1); Microcystins, Okadaic Acid, Endothall (inhibits PP2A); Cyclosporine A and FK 506/Immunophilin complexes, Cypermethrin; Cantharadin; Cantharidic acid; Deltamethrin (inhibits PP2B); bpV(phen), Dephostatin, mpV(pic), DMHV (Inhibits PTP); β-glycerophosphate; (−)-p-bromotertramisole oxalate; Fenvalerate; L-690,330; L-Homoarginine; Phenylarsine Oxide; Permethrin; Sodium molybdate (and permolybdate); Imidazole; Sodium fluoride; Sodium tartrate dehydrate; Sodium Stibogluconate; Sodium pyrophosphate; Suramin; Vanadate (orthovanadate and pervanadate); 1,4-Dimethylendothall; 1-nor-Okadaone; Allethrin; Ascomycin; Benzylphosphonic acid; Tautomycin; Tetramisole; and Tyrphostin 8.

As noted elsewhere herein, it is important to maintain a suitable balance of kinase and phosphatase inhibitors. For example, a suitable stabilizer can contain, as a phosphatase inhibitor, either sodium orthovanadate at a concentration of between about 100 mM and about 400 mM, or beta glycerophosphate at a concentration of between about 375 mM and 1.5M, and, as a kinase inhibitor, staurosporine at a concentration of between about 5.0 uM and 20.0 uM, or genistein at a concentration of between about 0.5 uM and 2.0 uM. A skilled worker can readily determine suitable ratios of other combinations of phosphatase and kinase inhibitors, in view of the preceding ratios.

The kinase and phosphatase inhibitors used in compositions and methods of the invention can function by any suitable mechanism. For example, a kinase inhibitor and/or a phosphatase inhibitor can directly inhibit the activity of the kinase or phosphatase enzyme; the kinase inhibitor can interfere with the kinase substrate, ATP; and/or the phosphatase inhibitor can interact with the phosphate group on a phosphorylated protein or act as a pseudo-substrate for the phosphatase.

Optionally, a stabilizer of the invention contains a protease inhibitor. As used herein, the term "protease inhibitor" refers to an agent which blocks the degradation of proteins, either from an end of the molecule or from an internal position. Protease inhibitors include a variety of proteinase inhibitors, e.g., inhibitors of serine proteinases (e.g. PNSF or aprotinin), cysteine proteases, aspartic proteinases, metalloproteinases (e.g. EDTA); acid proteinases, neutral proteinases, or alkaline proteinases.

Among the suitable protease inhibitors that can be used are, e.g., acetyl-Pepstatin; AEBSF, hydrochloride; ALLN; ALLM; Amastatin, *Streptomyces* sp.; E-amino-n-caproic acid (EACA); α1-antichymotrypsin; α2-antiplasmin; Antipain, dihydrochloride or hydrochloride; antithrombin III; α1-antitrypsin; p-APMSF, hydrochloride; aprotinin; ATBI; Benzamidine, hydrochloride; Bestatin; Bestatin, methyl ester; Calpastatin; CA-074; Calpeptin; carboxypeptidase; cathepsin inhibitor I, II, III; cathepsin B inhibitor I, II; cathepsin K inhibitor I, II, III; cathepsin L inhibitor I, II, III, IV, V, VI; cathepsin S inhibitor; Chymostatin; chymotrypsin inhibitor I; Cystatin; 3,4-dichloroisocouramin; diisopropylfluorophosphate (DFP); dipeptidyl peptidase IV inhibitor; 1,5-DNS-GGACK, 2HCl; dipeptidylpeptidase II inhibitor; E-64 protease inhibitor; Ecotin; EDTA; EGTA; elastase inhibitor I, II, III; EST; FUT-175; GGACK; HDSF; α-iodoacetamide; Kinnogen; Leuhistin; Leupeptin; α2-Macroglobulin; DL-2-Mercaptomethyl-3-guanidinoethylthio propanoic acid; NCO-700; Pepstatin A; phenylmethylsulfonyl fluoride (PMSF); PPACK; prolyl endopeptidase inhibitor; 2,3,5,7-tetranitro-9-fluorenone; TLCK hydrochloride; thrombin inhibitor; tripetidylpeptidase II inhibitor; trypsin inhibitor; Tyromycin A; and D-Val-Phe-Lys chloromethyl ketone, dihydrocholoride. Other protease inhibitors are disclosed, e.g., in Neel et al. (1997) *Curr Opin Cell Biol* 9, 193-204; and B. Goldstein (2002) *J Clin Endocrinol Metab* 87, 2474-2480).

A third component of a preservation composition of the invention is a permeability enhancing agent (sometimes referred to herein as a permeability agent or a permeation agent), which enhances the transport into a cell or tissue of a fixative and/or of a stabilizer. The permeability enhancing agent can, e.g., augment the penetration rate of the constituents of a composition of the invention through the tissue volume such that cells within the inner mass of the living tissue are rapidly reached and their molecules arrested for later diagnosis. The permeability rate of a stabilizer into a cell or tissue is a function of the proportion of cells to extracellular space, and the ratio of surface to volume for the tissue. Permeability of the tissue cell membrane to water, to the solute, and the diffusion coefficient of the solute in the extracellular space will all influence the permeability of the stabilization agent. Following mass transport and exchange between the intracellular and extracellular space, the preserving agent enters the cells.

A variety of permeability enhancing agents can be included in a composition of the invention. Among suitable permeability enhancing agents are polymers (such as PEG, polystyrene, etc.), proteins (such as lipophilic proteins), lipids, and nanoparticles (such as metallic or cyclodextrin nanoparticles). For example, suitable permeability enhancing agents include water; dimethysulphoxide (DMSO) at about 1.5 M; dimethylacetamide (DMAC); demethylformamide (DMF); dimethylsulphoxide (DCMS); fatty acids with $C_{10}$-$C_{18}$ saturated alkyl chains; sodium lauryl sulphate (SDS); sorbitan monolaureate 20; cetyltrimethyl ammonium bromide; nonoxynol surfactants; zwitterionic surfactants (e.g. dodecyl betaine); laurocapram: Azone (1-dodecylazacycloheptan-2-one); SR-38 (4-decycloazolidin-2-one); ethanolic solutions; essential oils, terpenes and terpenoids (eucalyptus, d-limonine, nerolidol, 1-8-Cineole, menthol); fatty alcohols (alknols); oleic acid; glycols; PEG 200 monolaureate; PEG 400 monooleate (Alkamuls 400-MO); PEG 400 monolaurate (Lipopeg 4-L); PEG 600 monooleate (Alkamuls 600-MO); PEG 6000 monooleate (Kesso Polyetheylene Glycol esters); polyoxyaryl ether (Syn Fac 8210); POE oleyl alcohol (Ethosperse OA-9); POE sorbitan monoleate (Atlas G8966T); POE myristyl ether (Lipco-4); POE lauryl alcohol (Ethosperse LA-4); POE lauryl ether (Brij 30); POE sorbitan monooleate (Glycosperse 0-5); POG lauryl sulphate (Emthox 5967); octyphenoxypoly (ethyleneoxy) ethanol (Igepal CA 420); linear alcohol ethoxylate (Rexonic N4); mono and diglycerides with polysorbate 80 (Tandem 8); nonyl phenol ethoxylate (Alkasurf NP-4); nonylphenoxypoly(ethyleneoxy) ethanol (Igepal CO-720); nonylphenol ethoxylate (alkasurf NP-15); castor oil ethoxylate (Sandoxylate C-32); ethoxylated cocmonoglyceride (Varonic LI-63); oleylalcohol condensed with ethylene oxide (Volpo-20); modified oxyethylated straight chain alcohol (Plurafac C-17); ethoxylated lanolin alcohol (Polychol 40); ethyoxylate polyoxypropylene glycols (Alkatronic PGP 23-7); ethyoxylate polyoxypropylene glycols (Alkatronic PGP 23-8); nonphenyl ethoxylate (Alkasurf NP-30); polyethylene 100 stearyl ether (Brij 700); monoglyceride and ethyl palmitate; alkylaryl polyether ethanol (Triton X-363 M); N,N-dimethyl amide (Mallcomid M 8-10); alkyl or aryl urea analogs; glycerol momlaureate and lauryl acetate; Sefsol-318 a medium chain glyceride; cell-penetrating peptides; pegylated peptides; cell penetrating peptides; polyethylene glycol monolaureate; phospholipids; pyrrolidones: N-methyl-2-pyrrolidone and 2-pyrrolidone; dendrimers; lectins; or pegylated and/or colloidal gold.

In one embodiment of the invention, the permeability agent is PEG, at a concentration of about 0.5-15%, e.g., about 0.5-5%. Higher concentrations of PEG can interfere with cellular histology and prevent tissues from being sectioned.

A permeability enhancing agent may be added as an independent element to a mixture of a fixative and a stabilizer of the invention, to form a preservative composition. In another embodiment of the invention, a stabilizer (one of more components thereof) of the invention is attached to (e.g., bound to, coupled to, immobilized on) to a permeability enhancing agent, which can facilitate the penetration of the stabilizing agent into a cell or tissue. Methods for attaching stabilizing agents to suitable permeability enhancing agents are conventional. In one embodiment, the elements of a stabilizer (e.g., a phosphatase inhibitor and a kinase inhibitor) and a permeability agent are both attached to a nanoparticle, which facilitates the entry of both types of components of a composition of the invention into a cell or tissue. The nanoparticles with the bound components may be suspended in a fixative of the invention.

A skilled worker will recognize that the relative amounts, or even the presence, of an individual component of a preservative composition invention, such as a permeability enhancing agent, may vary, depending on the individual cell type or specimen type. For example, some tissues (e.g. muscle tissue) are particularly dense and thus may require a larger amount of permeation enhancer than do less dense tissues. Alternatively, some tissues that comprise high levels of fat or hydrophobic layers (e.g. breast or skin) may require lower amounts of a permeation enhancer than do tissues lacking such a fatty nature. Such adjustments can be determined routinely, within the general confines of a preservative composition as discussed herein.

Physical methods can also be used to aid the penetration of a preservation composition of the invention into a cell or tissue. These methods include, e.g., pressure waves and permeabilization with grids of needles. Other physical methods include transient heat induction, for example by ultrasound, infrared, microwave, electric (high voltage), electromagnetic, RF (radiofrequency), or chemical methods. These physical methods both drive the preservation composition into the tissue and actively denature the proteins to inhibit kinase, phosphatase, and protease activity.

Other agents that can be present in a preservation composition of the invention include membrane receptor inhibitors, such as OSI-774 (Tarceva, Erlotinib); Traztuzumab (Herceptin); Lapatanib; and Gefitinib (Iressa). Antihistamines (H-1 receptor antagonists) that can be used include, e.g., Azatadine; Antazoline; Brompheniramine; Cyclizine; Chlorcyclizine; Cetirizine; Chlorphenir-amine; Clemastine; Cyproheptadine; Desloratadine; Dexchlorpheniramine; Dimenhydrinate; Diphenhydramine; Doxylamine; Fexofenadine; Hydroxyzine; Ketotifen; Loratadine; Mepyramine; Meclizine; Pheniramine; Phenindamine; Promethazine; and Triprolidine.

Other agents that can be present in a preservation composition of the invention include membrane stabilizing agents, which not only stabilize membranes, but also protect cells from injury until the cellular molecules and their post translational modifications are precipitated or fixed. Among suitable cell membrane stabilizers are, e.g., trehalose; carbohydrates; propylene glycol (e.g. at about 1.5 M); ethylene glycol (e.g. at about 1.5M); glycerol (e.g. at about 1.5 M); sucrose; glycine; chitosan or methylcellulose.

Other inhibitors of signal pathway activation that can be present in a preservation composition of the invention include agents that preserve cellular morphology, including organelle morphology for histologic examination, microdissection, and pathologic diagnosis following frozen section or polymer or paraffin sectioning. Suitable such agents include, e.g., polyethylene glycol (e.g. in a size range from about 200-8000 kD), chitosan, or methylcellulose.

Other agents that can be present include cross-linking agents (e.g., dialdehyde, gluteraldehyde, dithiobis-succinimidylpropionate, gum arabic, diethylene glycol, or gum arabic) and molecularly inhibited polymers or hydrogels such as N-isopropylacrylamide (NIPAm) and N,N'-methylenebisacrylamide (BIS) formed by precipitation polymerization.

Other agents that can be present in a preservation composition of the invention include ATPase inhibitors. Among the suitable ATPase inhibitors that can be used are, e.g., adenosine; amiloride hydrochloride; Bafilomycon A1, *Streptomyces griseus*; BHQ; (−)-Blebbistatin; (±)-Blebbistatin; BTS; Bufalin; 2,3-Butanedione 2-Monoxime; Calmidazolium chloride; cyclopiazonic Acid, *Pencillium cyclopium*; DPC (Dipehylamine 2-carboxylic acid); Eq5 inhibitor III, Demethylenastron; N-Ethylmaleimide; Folimycin, *Streptomyces* sp.; 4-Hydroxynonenal; Hypocrellin B, *Hypocrella bambusae*; Mastoparan; Mycalolide B, *Mycale* sp.; NC-1300-B; Oligomycin; Omeprazole; Quabain, Octahydrate; Phorbol-12,13-dibutyrate; Suramin, sodium salt; and Thapsigargin.

Of course, any of the components listed above as providing a particular function can fulfill one or more than one of the other functions described.

The preservative compositions (fixation/stabilization/permeability agents) described herein can preserve a variety of intracellular components. Although much of this application is directed to the preservation of phosphoproteins, it is to be understood that other cellular components (e.g., proteins that are not post-translationally modified; proteins that are post-translationally modified with moieties other than phosphate groups, such as, e.g., glycosyl, lipid or lipid-methyl groups; cellular organelles; etc.) can also be preserved by a method of the invention. In one embodiment, the compositions are added to whole blood in order to preserve labile cell surface antigen proteins. Because the surface proteins retain their antigenicity, the preserved cells can be further analyzed by methods that rely on antigenic surface antigens, such as cell sorting by FACS analysis or magnetic capture. See, e.g., Example V.

Any of a variety of conventional methods can be used to determine whether cellular signalling and/or metabolic function has been preserved by a composition of the invention. Physiochemical properties of an excised tissue can be measured, e.g., by immunohistochemistry, enzymology, microscopy, or biochemistry (see, e.g., the review article by Hernandez-Cueto et al. (2000) in *Am Journal Forensic Med. Path.* 21, 21-31. Among the enzyme histochemical markers that can be evaluated are: enzymes involved in mitochondrial oxidative enzyme activity, esterases, fibronectin, tenascin, e-selectin, p-selectin, TGF-α, TGF-β, interleukin 10, ICAM-1, VCAM-1, acid phosphatase, alkaline phosphatase, leucinaminopeptidase, and/or glycosaminoglycans. Among the biochemical analyses that can be carried out are the evaluation of: ATP and its decomposition products (ADP, AMP, IMP, inosine, hypoxanthine, xanthine, and uric acid). bromodeoxyuridine DNA synthesis, DNA and/or RNA polymerization, C3, immunoglobulins E, A, G, M, histamine, serotonin, cathepsin D, D-dimer, and/or lactate dehydrogenase. Analysis of the phosphorylation state of a protein can be carried out by conventional methods, e.g. as described herein.

The inventors have performed time course analysis of a variety of phosphoproteins, and have identified markers that exhibit a range of lability (e.g. loss or gain of the posttranslational modification, such as phosphorylation) following corporal excision. The phosphoproteins shown in Table 1 are "particularly labile" ("relatively labile") proteins. That is, the proteins change their phosphorylation state by more than 20% over time of storage in the preservative treatment, post tissue excision. The endpoints are organized in the table by cell signaling pathways. Although the particular phosphorylated amino acid residues which are noted in the table were used to monitor the phosphorylation state of the proteins in the table, other phosphorylated residues of the proteins may also be monitored.

TABLE 1

| Cell Signaling Pathway | Protein Kinase Endpoint |
|---|---|
| Stress/Inflammation | ASK-1 ser83 |
|  | IKBα ser32 |
|  | SAPK/JNK T183/Tyr185 |
| Adhesion/Cytoskeletal | B-Catenin ser33/37/Thr41 |
|  | Pak1 ser199/204/Pak2 ser192/197 |
|  | E-cadherin |
| Hypoxia/Ischemia | eNOS ser1177 |
|  | AcetylCoA Carboxylase ser72 |
|  | AMPK α1 ser485 |
|  | AMPK β1 ser108 |
|  | HSP90 |
| Proliferation | IRS-1 ser612 |
|  | GSK3α/β ser21//9 |
|  | AKT ser473 |
|  | AKT Thr308 |
|  | ERK Thr202/Tyr204 |
| Apoptosis | Cleaved Caspase 3 Asp175 |
|  | Cleaved Caspase 7 asp198 |
|  | BAD ser112 |
| Cell Cycle | Cyclin A |
| Transcription Factors | CREB ser133 |
|  | STAT1 Y701 |
|  | STAT3 Y705 |

One embodiment of the invention is a method for determining the preservation state of proteins (e.g. phosphoproteins) in a sample which comprises, e.g., a cell, tissue, bodily fluid or a product of a cell. The method comprises measuring the phosphorylation state of one or more endogenous surrogate markers (e.g., the highly labile endogenous surrogate markers of Table 1) in the sample. The method can be used to determine if the other proteins (e.g. phosphoproteins) in the sample are sufficiently well-preserved to be used for subsequent analysis, such as diagnostic molecular proteomic analysis, the study of the phosphorylation state of the proteins, etc.

Single endogenous surrogate markers may be used, or a plurality of such markers (e.g. between about 2-10, or more) may be used. In one embodiment of the invention, the surrogate markers from Table 1 that are used are the particularly labile phosphoproteins STAT-1 and/or STAT-3 (e.g., STAT-3), CC-3 (cleaved caspase-3) and ASK-1. The highly labile endogenous surrogate markers listed in Table 1 constitute an early warning of a compromised preservation state.

In addition to, or instead of, these phosphoproteins, other types of phosphoproteins may also be used. For example, suitable endogenous surrogate markers can be selected from a variety of classes of phosphoproteins, including those from specific pathways; classes of residues (e.g. tyrosine, serine or threonine); and nuclear, cytoplasmic, and cell membrane compartments. The endogenous surrogate markers may be in the form of a panel of selected phosphoproteins exhibiting different degrees of lability.

A variety of other types of endogenous surrogate markers may also be used, in addition to or instead of the phosphoproteins discussed above. For example, the endogenous surrogate markers may be non-phosphoprotein molecules whose stability is correlated with the state of preservation of phosphoproteins in the cellular population (e.g., lactate dehydrogenase, LDH, glucose-6 dehydrogenase, glucose oxidase and others).

In one embodiment, the endogenous surrogate markers comprise one or more of the phosphoproteins listed in Table 2, and/or one of more of p-selectin, e-selectin, IL-2, IL-6, IL-8, or fibronectin.

TABLE 2

Validated phosphoprotein endpoints and reference phospho-peptides.

| Antibody/Location | Function |
|---|---|
| Nucleus | |
| Apaf | A |
| *ATF-2 (Thr71) | B |
| *Aurora A/AIK (Thr288) | C |
| Catenin(beta) (Ser33/37/Thr41) | D |
| Catenin(beta) (Thr41/Ser45) | D |
| Chk1 (Ser345) | C |
| *Chk2 (S33/35) | C |
| *CREB (S133) | E |
| *CREB (S133) (1B6) | E |
| Elk-1 (S383) | E |
| *Estrogen receptor alpha (S118) (16JR) | E |
| *FKHR (S256) | C |
| FKHRL1 (S253) | C |
| *FKHRL1 (Thr32) | C |
| *MSK1 (S360) | G |
| PARP, cleaved (Asp214) | A |
| Cytoplasm | |
| *4E-BP1 (S65) | H |
| 4E-BP1 (T37/46) | H |
| *4E-BP1 (T70) | H |
| *Akt (S473) | H |
| *Akt (T308) | H |
| Akt1/PKB alpha (S473) (SK703) | H |
| *ASK1 (S83) | A |
| *c-Abl (T735) | G |
| c-Abl (Y245) | G |
| *Bad (S112) | G |
| *Bad (S136) | G |
| *Bad (S155) | G |
| *Caspase-3, cleaved (D175) | A |
| Caspase-6, cleaved (D162) | A |
| *Caspase-7, cleaved (D198) | A |
| *Caspase-9, cleaved (D315) | A |
| Caspase-9, cleaved (D330) | A |
| c-Raf (S338) (56A6) | F |
| *eIF4E (S209) | H |
| *eIF4G (S1108) | H |
| *eNOS (S1177) | I |
| eNOS/NOS III (S116) | I |
| *ERK 1/2 (T202/Y204) | F |
| Etk (Y40) | B |
| *FADD (S194) | A |

TABLE 2-continued

Validated phosphoprotein endpoints and reference phospho-peptides.

| Antibody/Location | Function |
|---|---|
| *FAK (Y397) (clone 18) | J |
| GSK3a (Ser21) (46H12) | H |
| GSK-3alpha (Y279)/beta (Y216) | H |
| *GSK-3alpha/beta (S21/9) | H |
| *IkappaB-alpha (S32) | K |
| *IkappaB-alpha (S32/36) (39A1431) | K |
| *Jak1 (Y1022/1023) | B |
| *Jak2 (Y1007/1008) | B |
| Lck (Y505) | F |
| MAPK (pTEpY) | F |
| *MARCKS (S152/156) | J |
| MEK1 (S298) | F |
| *MEK1/2 (S217/221) | F |
| *mTOR (S2448) | H |
| *mTOR (S2481) | H |
| *NF-kappaB p65 (S536) | A |
| *p38 MAPK (Thr180/Y182) | F |
| p70 S6 Kinase (S371) | H |
| *p70 S6 Kinase (T389) | H |
| *p70 S6 Kinase (T412) | H |
| p90RSK (S380) | F |
| *PAK1 (S199/204)/PAK2 (S192/197) | J |
| PKA C (T197) Monoclonal | E |
| PKC (pan) (betaII S660) | E |
| PKC alpha (S657) | E |
| PKC alpha/beta II (T638/641) | E |
| PKC delta (T505) | E |
| PKC theta (T538) | E |
| PKC zeta/lambda (T410/403) | E |
| PKR (T446) | H |
| *PTEN (S380) | J |
| Pyk2 (Y579/580) | J |
| Pyk2 (Y881) | J |
| *Pyk2 (Y402) | J |
| *Ras-GRF1 (S916) Monoclonal | F |
| *SAPK/JNK (T183/Y185) | A |
| Shc (Y239) | F |
| *Shc (Y317) | F |
| Smac/Diabolo | G |
| *Smad2 (Ser465/467) | F |
| *Src (Y527) | F |
| Src Family (Y416) | F |
| STAT1 (Ser727) | B |
| *STAT1 (Y701) | B |
| *STAT3 (Ser727) | B |
| *STAT3 (Y705) | B |
| STAT3 (Y705) (9E12) | B |
| *STAT5 (Y694) (14H2) | B |
| *STAT5 (Y694) | B |
| *STAT6 (Y641) | B |
| XIAP | G |
| Zap-70 (Y493) | E |
| Membrane | |
| Adducin (Ser662) | J |
| c-Kit (Y703) | F |
| c-Kit (Y721) | F |
| *c-Kit (Y719) | F |
| EGFR (Y845) | G |
| EGFR (Y992) | G |
| EGFR (Y1045) | G |
| EGFR (Y1068) | G |
| EGFR (Y1148) | G |
| EGFR (Y1173) (9H2) | G |
| EGFR (Y1173) | G |
| *ErbB2/HER2 (Y1248) | G |
| *IGF-1 Rec (Y1131)/Insulin Rec (Y1146) | H |
| *IRS-1 (S612) | H |
| PDGF Receptor Beta (Y751) | I |
| PDGF Receptor beta (Y716) | I |
| *PDGF Receptor beta (Y751) | I |
| VEGF Receptor-2 (Y1175) | I |
| *VEGFR 2 (Y951) | I |
| VEGFR 2 (Y996) | I |

TABLE 2-continued

Validated phosphoprotein endpoints
and reference phospho-peptides.

| Antibody/Location | Function |
|---|---|
| Mitochondria | |
| Bak | A |
| Bax | A |
| Bcl-2 (S70) | G |
| *Bcl-2 (T56) | G |
| Bcl-XL | G |

\* = phosphopeptide available
A = Apoptosis
B = Transcription/Cytokine Production/Apoptosis
C = Cycle Cycle Control
D = Migration/Adhesion
E = Transcription/Proliferation/Differentiation
F = Growth/Differentitation
G = Pro-Survival/Proliferation/Apoptosis
H = Growth/Translation/Glucose Metabolism
I = Angiogenesis/Nitric Oxide synthesis
J = Motility/Adhesion/Cytoskeletal structure
K = Proteasome degradation Markers that are labile at early, intermediate or late times after removal of a sample from a subject, in the absence of preservation, can be used.

Other endogenous surrogate markers that can be used are markers of inflammation. Excised tissue is essentially wounded, or traumatized tissue, in respect to activation of cell signaling pathways. Wound vitality has been well characterized in forensic pathology. Stages of wound healing typically follow 4 pathways: inflammation, angiogenesis, epithelialization, and tissue remodeling. Excised tissue therefore is expected to have similar stages of cell signaling activation based on trauma, environmental stress, hypoxia, prosurvival signals, and apoptotic signals. Suitable endogenous surrogate markers of inflammation include, for example:

Cell-cell adhesion—PAX, Src, FAK, p130cas, Cofilin, fibronectin, actin, ICAM-1, VCAM-1, e-Selectin, p-Selectin;

Cytokines—TNFα, Interleukin-1 (IL-1), IL1β, IL-6, IL-8, p38MAPK, ERK, SAPK/JNK, IKK, IkB, NFKβ;

Surrogate markers of stress: IL-6, iNOS, eNOS, Jak1/2, Stat3, Stat5, Stat1, Shp2, Grb2, MEK, ERK;

Surrogate markers of hypoxia: HIF-1α, AMPKα, AMPKβ, AMPKγ, PKA, LKB1, AcetylCoA Carboxylase, cytochrome c, COX2;

Surrogate markers of prosurvival: AKT, mTOR, 4EBP1, p70S6, eIF4G, eIF4E, GSK3β;

Surrogate markers of apoptosis: Annexin, TNFα, AKS-1, IKK, IkB, NFKB, Caspases 3, 6, 7, 9, INK, Bcl-2, BCL-XL, Bax, Bak, Bad, Smac/Diablo, Apaf-1, Cytochrome c, Lamin A.

The measurement of endogenous surrogate markers is particularly useful for determining the preservation state of a sample when the use of a sentinel, as described below, is not possible. For example, a sentinel may not be available, or the tissue to be analyzed is archival tissue, to which a sentinel was not added after removal of the tissue from a body.

Another aspect of the invention is a sentinel (an exogenous sentinel), which can be used to monitor the preservation state of proteins in a sample at two different time points. A sentinel of the invention comprises a particulate entity to which is attached (associated, bound, immobilized) one or more of the (endogenous) surrogate markers discussed herein. Because the markers, when attached to a sentinel, are no longer "endogenous," they are sometimes referred to herein as "surrogate markers," or "surrogate phosphoproteins." Any of the surrogate markers discussed herein, or other suitable markers that will be evident to a skilled worker, may be attached to a sentinel of the invention.

The particulate entity can be any entity that can be contacted with a sample at a first time, then removed from the sample at a second time for the determination of the preservation state (e.g. the phosphorylation state) of the protein marker(s) attached to the sentinel. For example, the particulate material can be made of hydrogel, silicon, a porous inert clay, polystyrene or other polymer, or colloidal gold. In one embodiment, the particulate material is a nanoparticle, such as a cyclodextrin or metal nanoparticle (e.g., a magnetic nanoparticle). The sentinel can be removed from the sample by any of variety of methods. For example, it can be centrifuged (spun out of the sample), or separated by size or by the use of a suitable tag. Magnetic nanoparticles can be isolated from cellular lysates of a specimen via magnetic depletion.

A sentinel may be used to monitor the stability of proteins in a sample between the time the sample is removed from a subject and the time it is to be subjected to a procedure, such as molecular characterization. Then, the presence or absence, or level, of the phospho groups on a surrogate marker that is attached to a sentinel can be measured and compared to the level when the sentinel was first introduced into the specimen, in order to evaluate the processing history. Through this objective standard, the impact of processing variables on the tissue phosphproteome can be measured as part of laboratory specimen quality control assessments. In one embodiment, a sentinel is used to determine the amount of time between the removal of the sample from a subject and the start of a procedure (e.g., a fixation/preservation procedure).

The sample can be, e.g., a cell, tissue, bodily fluid or product of a cell.

One aspect of the invention is a method for determining the preservation state of proteins in a sample (e.g. a sample which comprises a cell, tissue, bodily fluid or product of a cell) at two different time points. The method comprises contacting the sample at the first time point with a sentinel attached to (associated with) one or more surrogate markers, such as the highly labile phosphoproteins that are discussed herein; removing the sentinel from the sample at the second time point (e.g., under conditions that will not interfere with subsequent analysis of the proteins in the sample); removing the sentinel from the sample; and measuring and comparing the phosphorylation state of the proteins attached to (associated with) the sentinel at the two time points.

The term, "a" sentinel, as used herein, includes one or more sentinels. For example, single sentinels may be used, or a plurality (e.g., a panel) of sentinels may be used, which can be the same or different. Each sentinel may contain one or more surrogate markers, which can be the same or different.

In one embodiment, the sample comprises a cell or tissue, and the method comprises contacting the cells in the sample with a sentinel at a first time point (e.g., under conditions effective for the sentinel to enter the cells); removing the sentinel from the cells in the sample at a second time point (e.g. under conditions that will not interfere with subsequent analysis of the proteins in the sample); and analyzing and comparing the phosphorylation level of surrogate marker(s) on the sentinel at the two time points. The sentinel may be introduced into a cell in the presence of a permeation agent.

Figure 9:
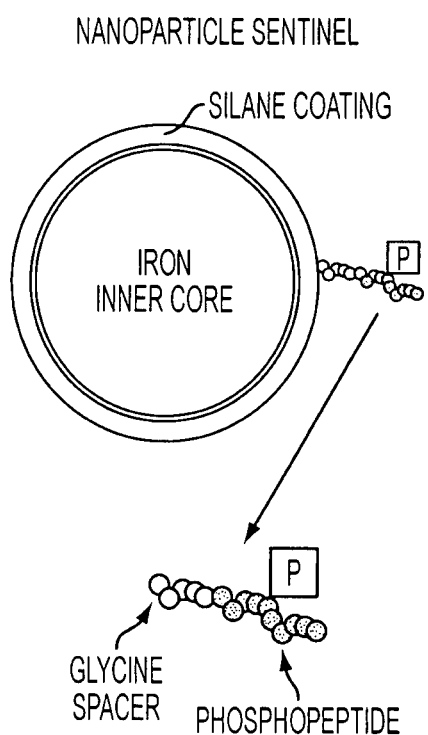
FIG. 9 shows a nanoparticle sentinel.

In one embodiment, one or more sentinel molecules are added to a sample at a time point prior to processing, such as the time of collection; and, following the processing, the sentinel(s) are removed from the sample and characterized (e.g., the phosphorylation state of the molecules is analyzed). See Example IV and FIG. 9 for a further discussion of sentinels of the invention.

In one embodiment, the phosphoproteomic endpoints that are present on sentinels are particularly labile and have short half-lives (e.g., phosphoproteins selected from phosphoproteins in Table 1). As used herein, the term "phosphoprotein" includes polypeptides of any suitable size, including phosphopeptides. One or more (e.g., 2, 5, 10 or more) of these endpoints can be incorporated into a sentinel (e.g., nanoparticle sentinel) in order to generate a chemically defined sentinel (nanoparticle sentinel) that can be produced on a large scale.

Nanoparticles can be injected into living tissues and infiltrate them (see, e.g., Muldoon et al. (1995) Am J Pathol 147, 1840-1851). For example, it has been shown that monocrystalline iron oxide nanoparticles (5 nm in diameter with an outer core of dextran, creating an overall particle size of roughly 20 nm) can be injected into rat brains, where the particles permeate the brain cortex over a span of roughly 7.93 mm, a distance many times greater than the size of the particle.

Conventional methods can be used to make sentinels (e.g., nanoparticle sentinels) of the invention and to attach suitable marker proteins to them. Surrogate protein markers may be attached (associated with, bound to, immobilized on) a sentinel (e.g. nanoparticle) by conventional methods, such as via a linker. For example, magnetic iron nanoparticles with a silane coating can be derivatized through the addition of NHS functional groups. This provides a linkage site for the amino terminus of synthesized peptides. A collection (e.g. about 1, 2, 5, 10 or more) of phosphopeptides that function as sentinels are synthesized (e.g. to a purity of about 95%). The peptides may contain an amino terminal stretch of glycines, which serve as spacer elements. Antibodies are available that specifically recognize the phosphorylated form of these peptides. Many such antibodies have been validated for monitoring the phosphorylation state of phosphoproteins.

In one embodiment of the invention, a single specimen container (e.g., a conventional mesh bag or pouch that is typically used to store biopsy samples) is pre-filled with a combination of a preservative composition of the invention and one or more sentinels. Immediately upon excision in the operating room (O.R.) or outpatient clinic, a tissue specimen is placed in the specialized container. The container and specimen are stable at room temperature during transport or shipping. Within a clinical laboratory, the sentinel additive may be applied to gather quality assurance data for the processing and analysis phases and to support regulatory (College of American Pathologists [CAP]/Clinical Laboratory Improvement Act [CLIA]) standards. Nevertheless, the preservative and sentinels do not alter the gross examination, histology, or morphology, and maximize the yield of quantitative protein endpoints. Following removal of the tissue from the container, measurement of endogenous surrogate endpoints can be used to qualify acceptance of the specimen for, e.g., molecular analysis or banking.

In one embodiment of the invention, the mesh pouch is impregnated with unstable components of a preservative composition of the invention, such as proteinaceous components, including proteinaceous inhibitors of kinases or phosphatases; these unstable components are then dried, which allows them to have a longer shelf life than if they were stored in a liquid form. After a sample has been placed in the mesh pouch, the remaining liquid components of the preservation solution are added to the pouch, thereby reconstituting the preservation solution, and allowing the sample to be fixed and stabilized.

In another embodiment, the mesh pouch is impregnated with a compound that, when contacted with a sample and/or a preservative solution of the invention, releases a short, intense burst of heat, raising the temperature greater than 65 degrees C. within 1-15 minutes, thereby denaturing the tissue and aiding in its preservation. The heat generating compound can be any dried agent known in the art to generate an exothermic reaction, such as chemicals used in hand warmers and stove-free cooking (e.g., potassium permanganate, manganese oxide, potassium chlorate, barium peroxide, potassium nitrate, metals, semimetals, metal alloys or metal-semimetal alloys).

Another aspect of the invention is a kit useful for any of the methods disclosed herein. Such a kit may comprise a composition of the invention (e.g. for fixing and stabilizing proteins in a sample); reagents, such as specific antibodies, for measuring the amount of phosphorylation of an endogenous surrogate marker of the invention, or of a surrogate marker on a sentinel; and/or a sentinel of the invention. A kit of the invention may further comprise a (one or more) container or packaging material. Kits of the invention can be used, e.g., for preparing samples from a subject for further analysis, for banking, or for experimental applications. A skilled worker will recognize components of kits suitable for carrying out any of the methods of the invention, or others.

Optionally, the kits comprise instructions for performing the method. Optional elements of a kit of the invention include suitable buffers, pharmaceutically acceptable carriers, or the like, containers, or packaging materials. The reagents of the kit may be in containers in which the reagents are stable, e.g., in lyophilized or dried form or as stabilized liquids. The reagents may also be in single use form, e.g., for the preservation of a single patient sample, or of multiple samples from a single patient.

The components of a preservation composition of the invention that are present in a kit may be in a liquid form, a dried form, or both. To protect against degradation, the labile components (e.g., proteinaceous components) may be in a dried form, and the remaining components in a liquid form. The dried components may form a coating on a surface, and they may be reconstituted by contact with a liquid comprising the remaining components of the composition.

Another aspect of the invention is a device for collecting and preserving a cellular or tissue specimen from a subject, comprising a first chamber that excises or procures a specified volume of sample (e.g. a needle), connected to a second chamber that contains a preservative composition of the invention, such that with a single operation the sample is procured and immersed in the preservative in the chamber containing the preservative composition. In one embodiment, the second chamber is removable, and can be used directly for tissue sectioning, molecular processing, or the like. For example the second chamber can be a multi purpose vessel for storage and mailing of the preserved tissue; and/or it can contain an outlet region which can directly interface with an automated or semi-automated system for tissue sectioning In the foregoing and in the following examples, all temperatures are set forth in uncorrected degrees Celsius; and, unless otherwise indicated, all parts and percentages are by weight.

EXAMPLES

Example I

Materials and Methods

A. Reverse Phase Protein Arrays (RPA)—Quantitation of Phosphoproteins in Tissues and Cells.

The RPA format, originated by the present inventors and collaborators (see, e.g., Paweletz et al. (2001) *Oncogene* 20, 1981-1989), immobilizes an individual test sample in a miniature dilution curve such that an array contains hundreds of different patient samples, treatments, or time points. In the RPA format, each array is incubated with one detection protein (e.g. anti-peptide antibody), and a single analyte endpoint is measured and directly compared across multiple samples. Briefly, the lysates are printed on glass backed nitrocellulose array slides (FAST Slides Whatman, Florham Park, N.J. or ONCYTE slides Grace BioLabs, Bend, Oreg.) using a robotic array printing device (GMS 417 arrayer (Affymetrix, Santa Clara, Calif. or Aushon 2470, Aushon Biosystems, Burlington, Mass. equipped with 125-500 µm pins). Each lysate is printed in a dilution curve representing neat, 1:2, 1:4, 1:8, 1:16 and negative control dilutions. The slides are stored with desiccant (Drierite, W. A. Hammond, Xenia, Ohio) at −20° C. prior to immunostaining.

To date we have 150 validated antibodies recognizing a wide variety of analytes (see, e.g., Gulmann et al. (2005) *Clin Cancer Res* 11, 5847-5855; Sheehan et al. (2005) *Mol Cell Proteomics* 4, 346-355; Davidson et al. (2006) *Clin Cancer Res* 12, 791-799; Nishizuka et al. (2003) *Proc Natl Acad Sci USA* 100, 14229-14234; Petricoin et al. (2005) *J Clin Oncol* 23, 3614-3621; Wulfkuhle et al. (2003) *Proteomics* 3, 2085-2090) and Table 2).

B. Protein Microarray Immunostaining.

Immunostaining is performed on an automated slide stainer per manufacturer's instructions (Autostainer CSA kit, Dako, Carpinteria, Calif.). Each slide is incubated with a single primary antibody at room temperature for 30 minutes. Polyclonal primary antibodies can be, e.g.: GSK3α/β Tyr279/216 (Invitrogen-Biosource, Carlsbad, Calif.), BCL-2, HIF-1α (BD, Franklin Lakes, N.J.), 4EBP1, FKHR ser256, eIF4E, eIF4E ser209, eIF4G, eIF4G ser1108, IGFR-β, IRS-1, IRS-2, IRS-1 ser612, SGK, Bak, Bax, BAD, BAD ser112, BAD ser136, BAD ser155, B-Raf, mTOR, mTOR ser2448, p70S6 Thr389, p70S6 kinase, p70S6 ser371, S6 kinase ser240/244, Akt, Akt ser473, Akt Thr308, 4EBP1 ser65, 4EBP1 ser70, and 4EBP1 Thr37/46 (Cell Signaling Technology, Danvers, Mass.). A negative control slide is incubated with antibody diluent. Secondary antibody can be goat anti-rabbit IgG H+L (1:5000) (Vector Labs, Burlingame, Calif.).

C. Bioinformatics Method for Microarray Analysis.

Each array is scanned, spot intensity analyzed, data normalized, and a standardized, single data value can be generated for each sample on the array (Image Quant v5.2, GE Healthcare, Piscataway, N.J.) or MicroVigene v2.8, Vigene Tech, Billerica, Mass.). Spot intensity is integrated over a fixed area. Local area background intensity is calculated for each spot with the unprinted adjacent slide background. This results in a single data point for each sample, for comparison to every other spot on the array. The Ward method for two-way hierarchical clustering can be performed using JMP v5.0 (SAS Institute, Cary N.C.). Wilcoxon two-sample rank sum test can be used to compare values between two groups. P values less than 0.05 are considered significant. When one cannot assume a normal distribution of the variables, non-parametric methods are used. Kaplan-Meier (log-rank) survival estimates for univariate survival analysis can be used.

Example II

Human Tissue Phosphoprotein Stability Time Course Analysis (in a "Real-World" Hospital Setting)

RPA microarray technology was employed to conduct a time course analysis of phosphoprotein residue end points on tissue procured from the following large tissue specimens: a) non-diseased uterus endometrium and myometrium, b) uterine leiomyomas, c) unaffected colonic mucosa and submucosa, d) unaffected lung and e) lung adenocarcinoma. Special emphasis was placed on the time period taking place immediately following procurement from the patient, e.g. 5 minutes, 10 minutes and 20 minutes, as a means to bracket the "time zero" window. This was done so that the earliest changes due to cooling of the tissue from 37° to room temperature could be observed. For uterus, we also sampled extended time points out to 90 minutes. End points were chosen to span growth factor receptor, pro-survival, and stress pathway related proteins (FIG. 2). The cellular content of each time point sample represented the volume of a sixteen gauge core needle biopsy. Twenty serial frozen sections cut at 8 microns were processed and lysed. Each signaling protein endpoint was normalized to total cellular protein content. All endpoints have been previously validated for yield, linearity, and precision (Sheehan et al. (2005), supra). Changes in phosphoprotein endpoint levels were expressed as a percent of the quantitative value measured at the immediate point of tissue procurement.

Results.

1) Yield: The tissue cellular volume obtained was highly adequate, such that each phosphoprotein endpoint was measured in a range that was much greater than ten-fold above background (value without primary antibody) and was within the linear range of the assay. Less than five percent of the 150 uL volume for each tissue sample time point lysate was used to analyze the 12 endpoints displayed in FIG. 2. 2) Stability Time Course: As shown in FIGS. 2A-2E, immediately upon procurement, fluctuations occurred in the selected phosphoprotein targets. Some endpoints transiently increased over time, while others exhibited a slow decline. The phosphoproteins shown in FIGS. 2A-2E represent typical members of a panel of endogenous surrogates that can be used to judge the stabilization condition of the tissue. In one embodiment of the invention, an investigator determines if a sample of interest (e.g. comprising a cell or tissue) is in an adequate state of preservation to be subjected to molecular diagnostic analysis. In another embodiment, an investigator can determine for how long a period a sample of interest has been removed from a subject. In this embodiment, the investigator compares the phosphorylation state of one or more of the endogenous phosphoproteins to a calibration curve indicating the phosphorylation state of the protein over time. The data presented here support the feasibility of the proposed surrogates and the suitability of the chosen methods.

Figure 1:
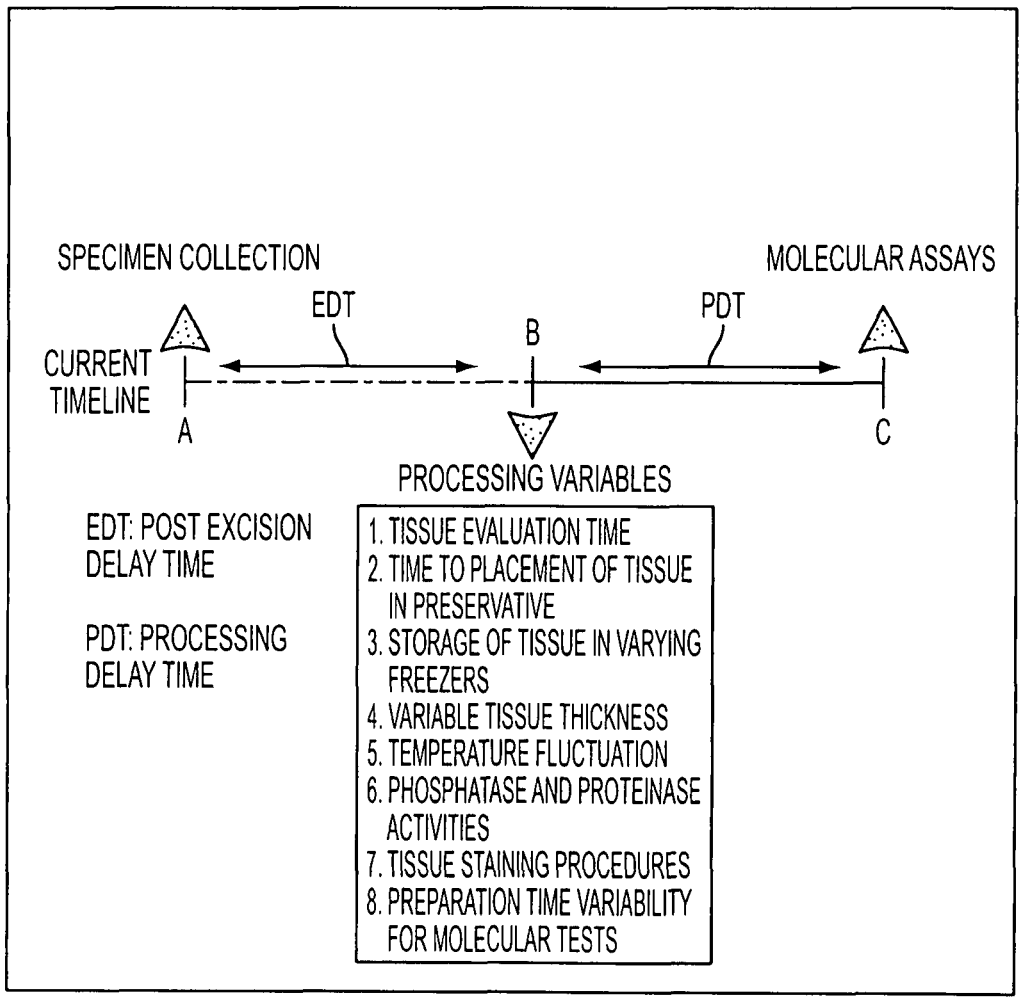
FIG. 1 shows variable time periods that define stability intervals for human tissue procurement.
Figure 2A:
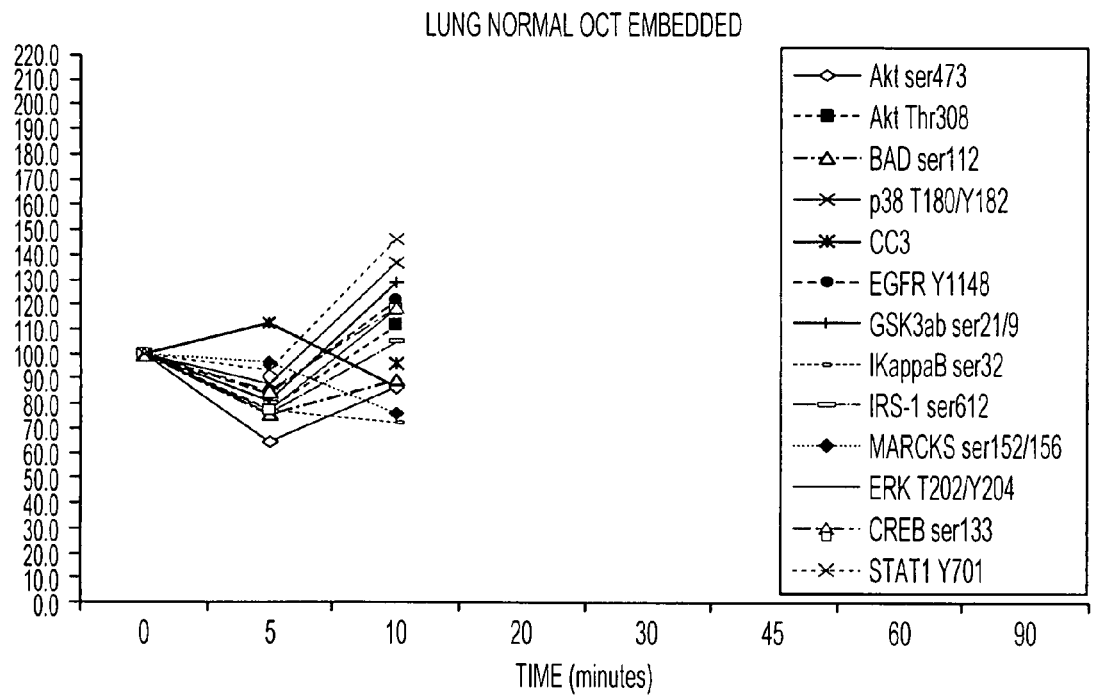
FIG. 2 shows a protein stability time course of tissue after procurement prior to preservation. The figure shows the change or fluctuation in phosphoproteins over time compared to a baseline, which is the level of that same phosphoprotein in tissue frozen at the time of excision. Freezing to obtain the time zero baseline was conducted either by snap freezing in liquid nitrogen or freezing in OCT cryoprotectant gel, a conventional procedure for cutting frozen sections. Freezing the tissue samples at each series of time points arrested any changes taking place in the tissue compared to the tissue allowed to remain in a living state at room temperature. The remainder of the tissue sample was allowed to sit at room temperature for varying amounts of time, without further preservation. The figure shows a time course, in which values from the unpreserved time course are compared to the values of the sample preserved immediately after excision. The endpoints evaluated represent pro-survival, apoptotic, and transcription control proteins/phosphoproteins.
Figure 2B:
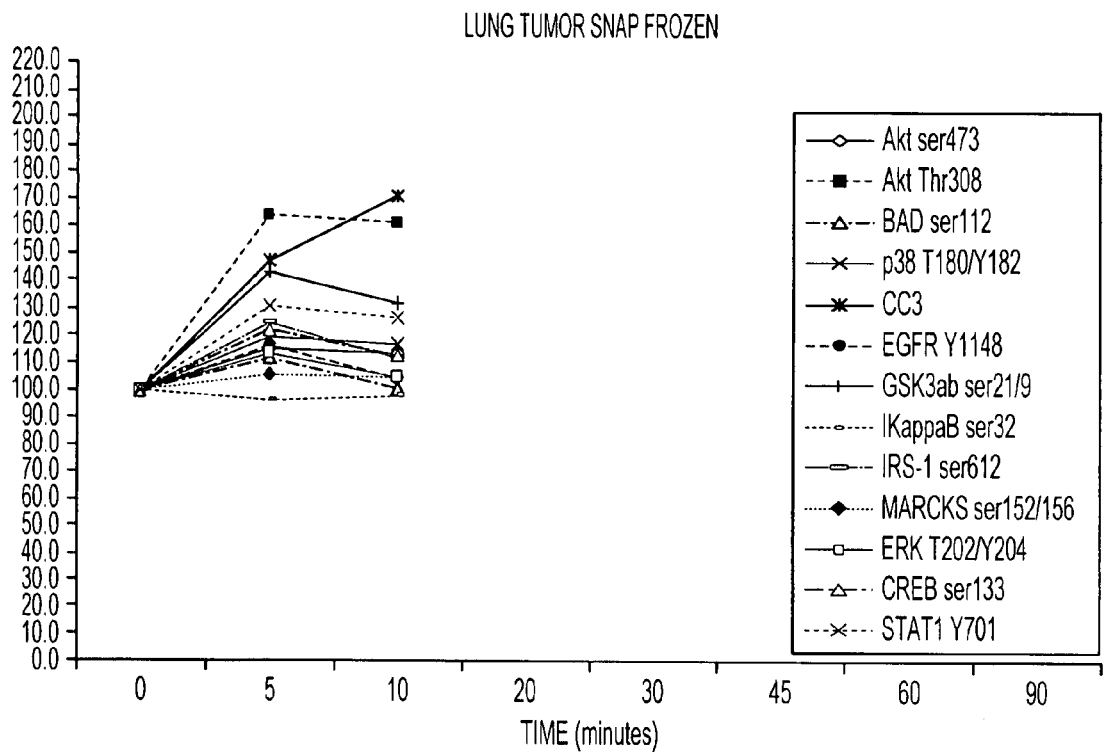
Figure 2C:
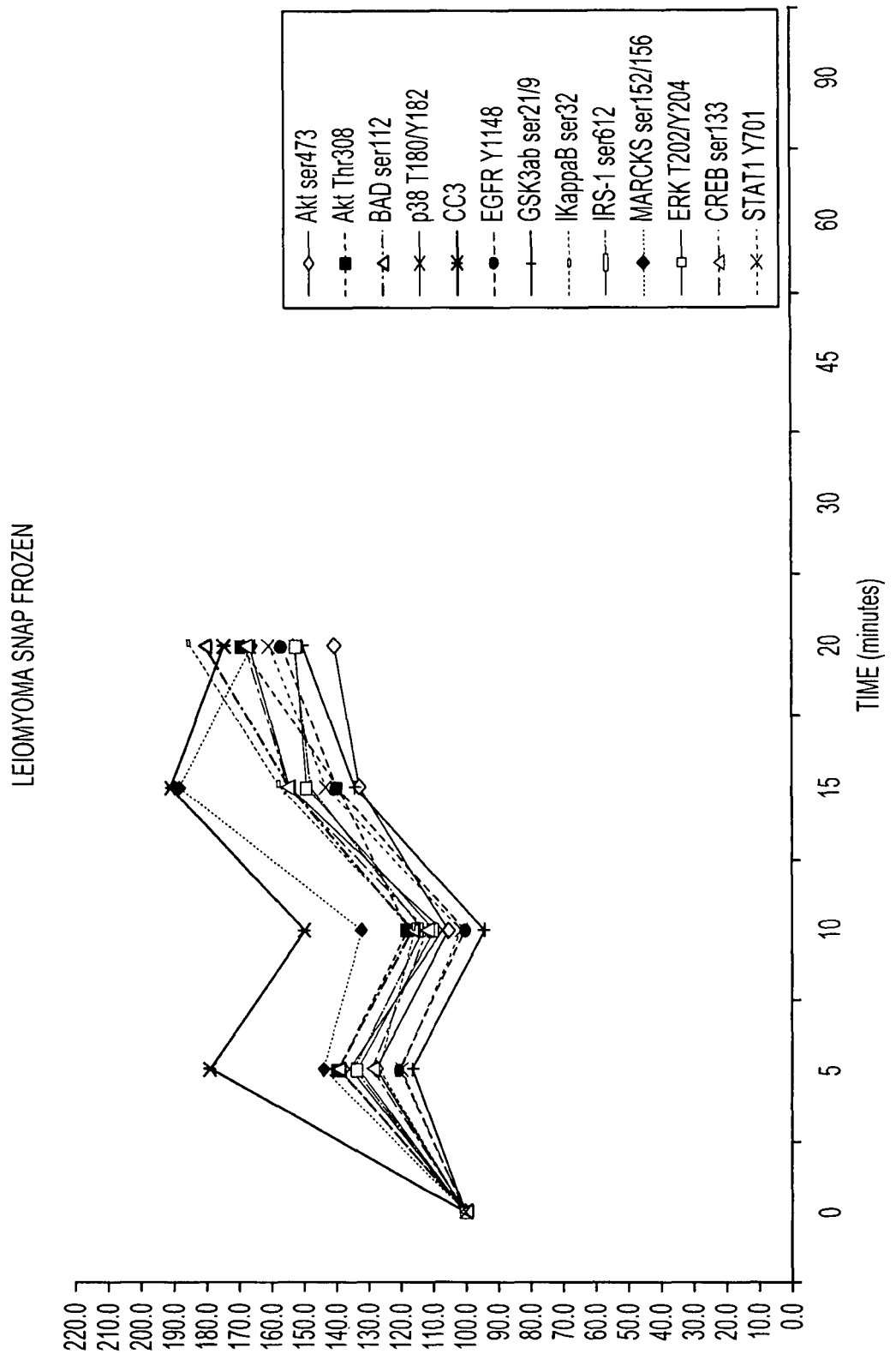
Figure 2D:
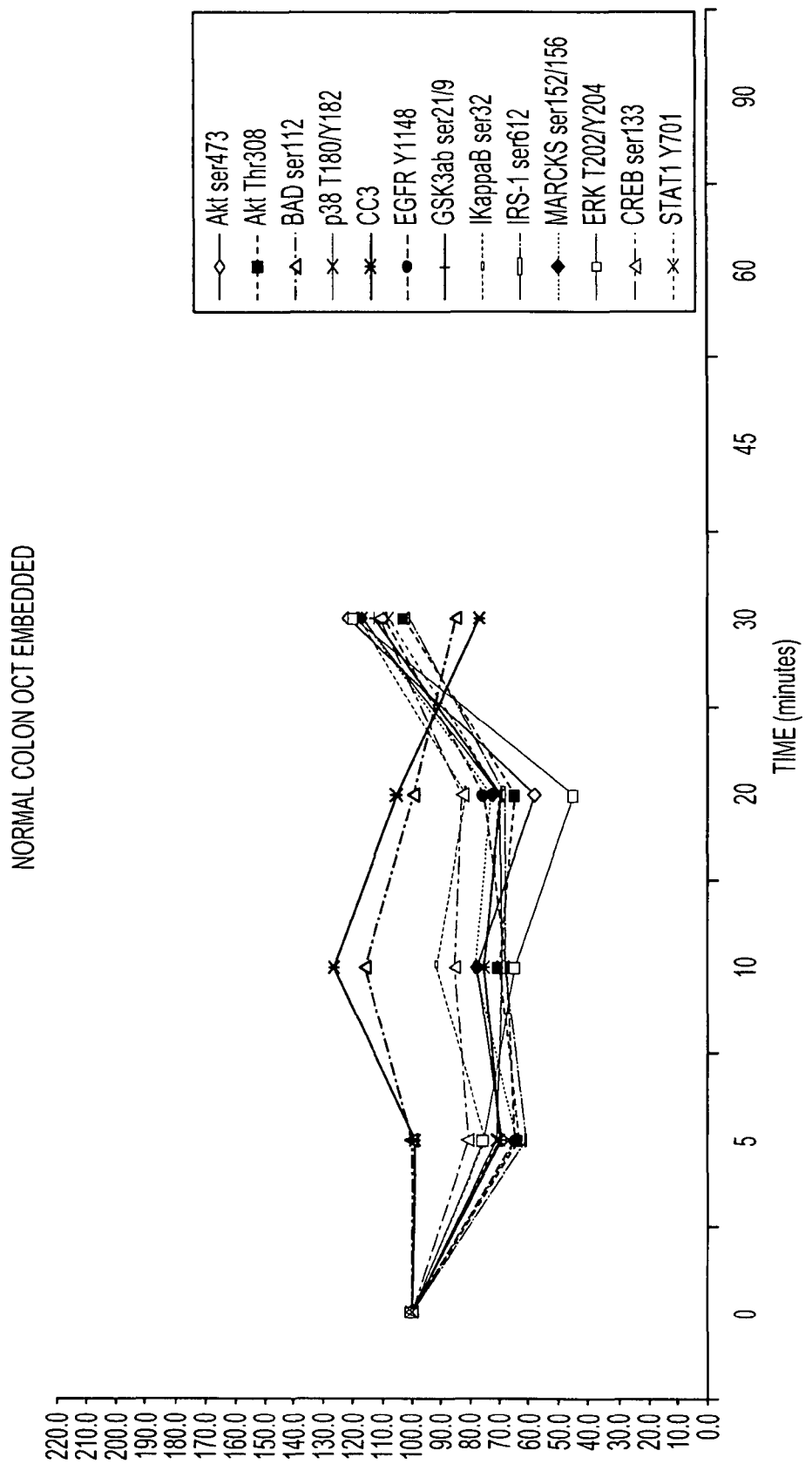
Figure 2E:
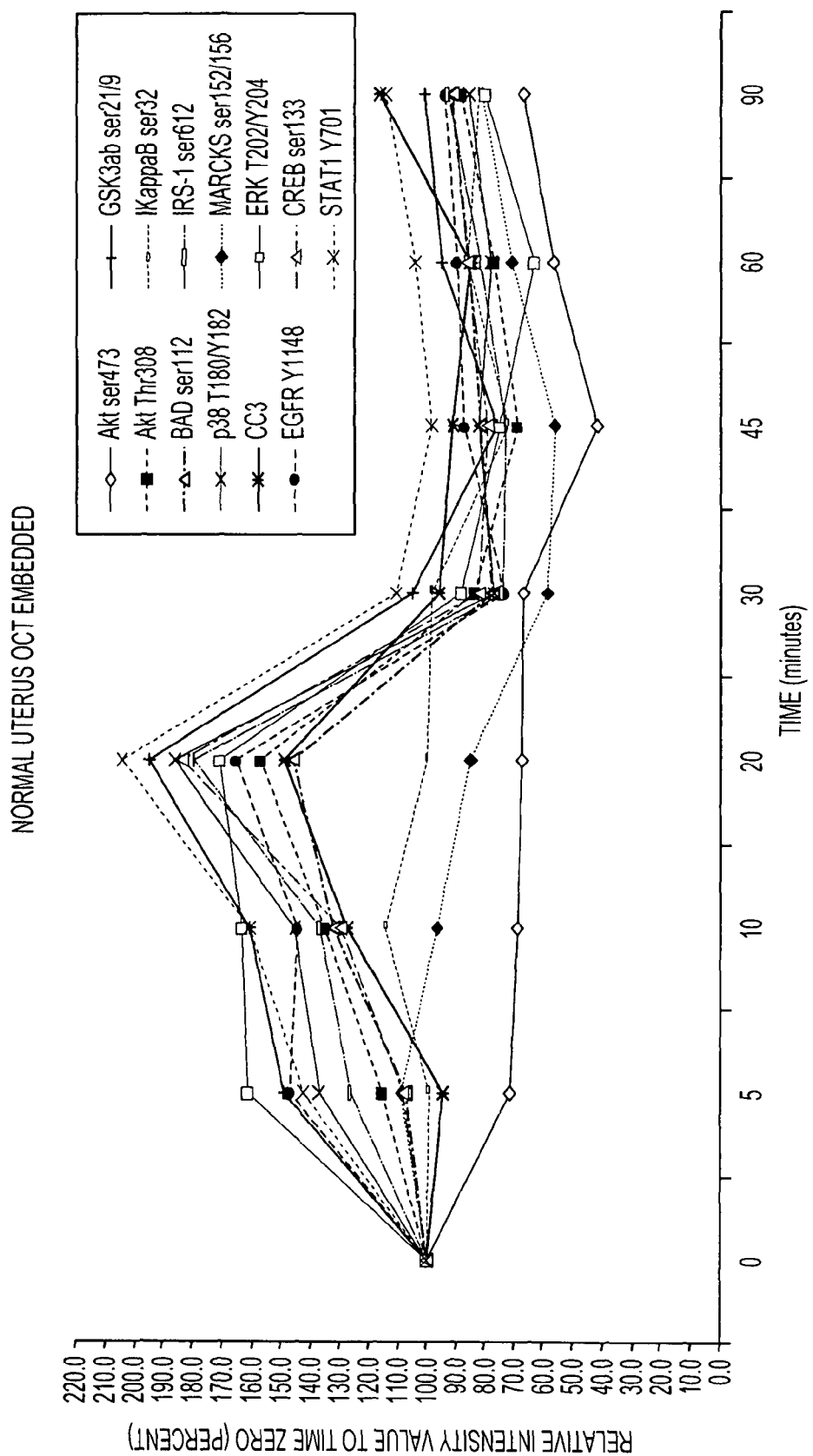
Figure 3A:
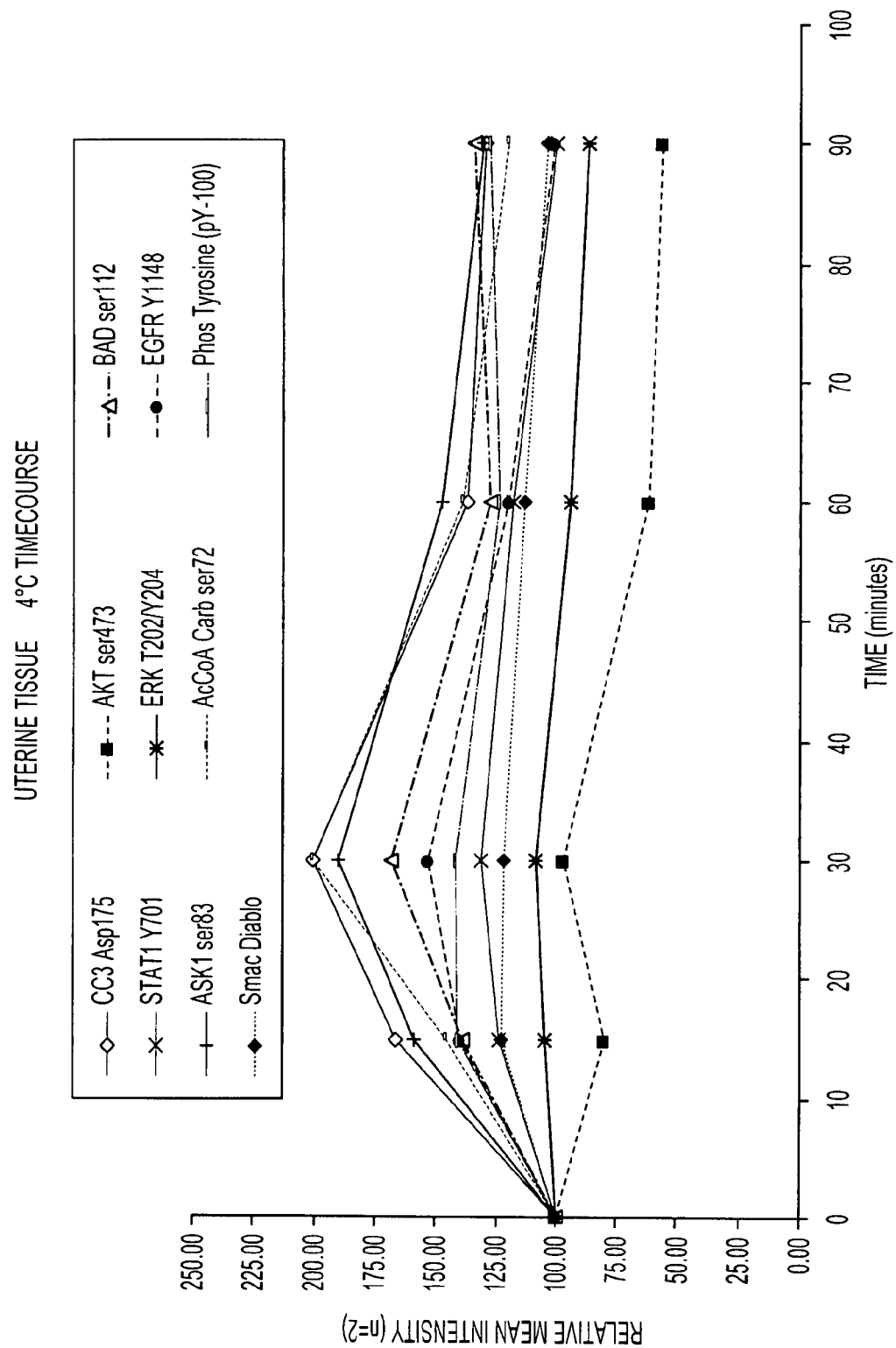
FIG. 3A shows the time course at 4° C.
Figure 3B:
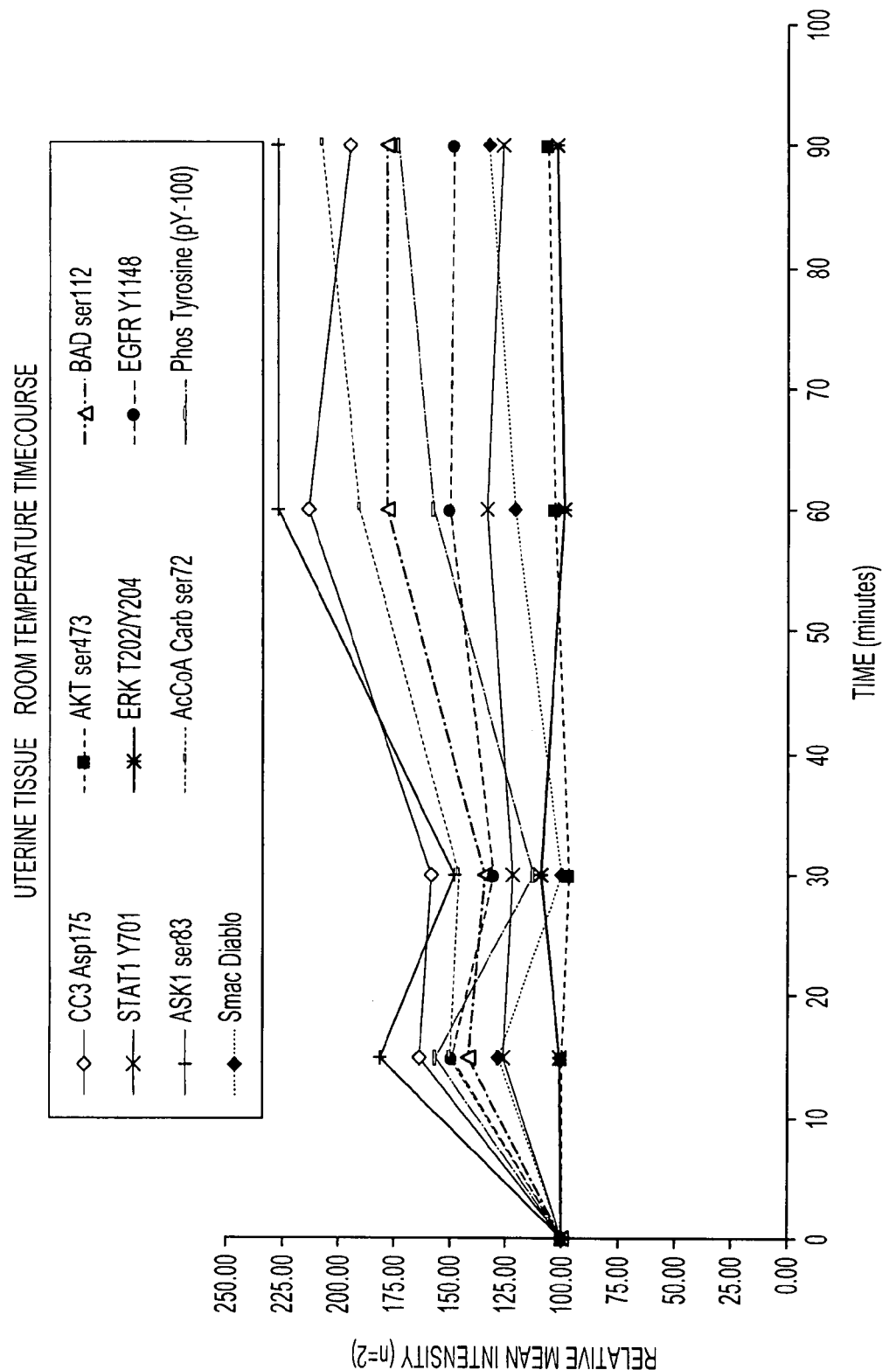
FIG. 3B shows the time course at room temperature. Selected phosphorylated proteins in pro-survival and apoptotic pathways that exhibited the greatest fluctuation, both positive and negative, over time, constitute example candidate surrogate markers.

Further time courses were conducted as above, except that only uterine tissue was examined, and the end points chosen were within the prosurvival, stress and apoptosis pathways. The design of the time course at room temperature and at 4° C. are shown in FIG. 3. The changes in phosphorylation state were slowed at 4° C. but were not abolished. It is evident from the time courses presented in the Examples which endogenous markers can serve as surrogate markers for a variety of uses.

Example III

Identification of Tissue Phosphoprotein Stabilizers

Figure 4A:
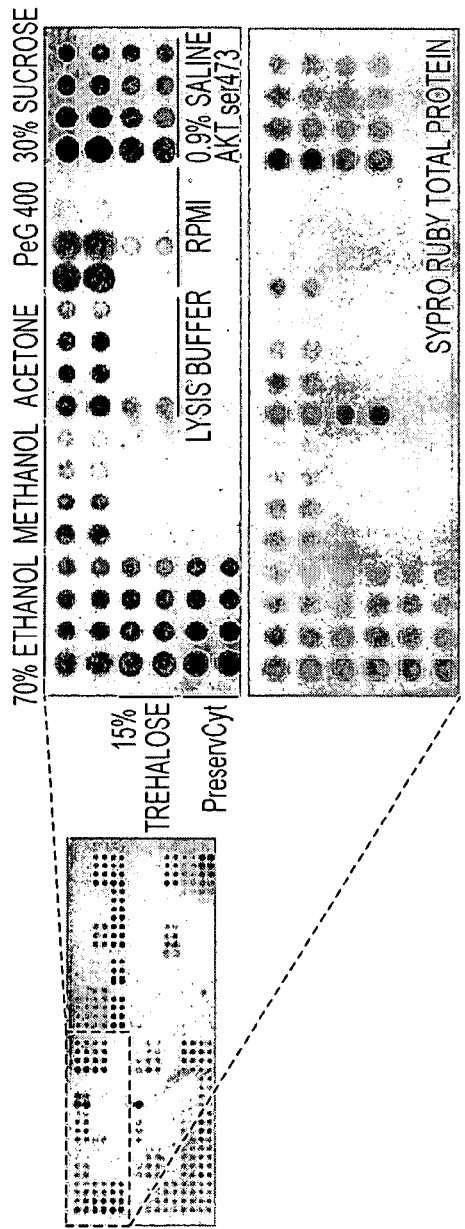
FIG. 4A shows an image of a microarray stained with AKT ser473 (top right) and Sypro Ruby (bottom right) for assessment of phosphorylated protein levels (AKT ser473) and overall protein yield (Sypro Ruby) per sample after the samples were incubated in various chemical solutions. Each set of 4 horizontal spots by 2 vertical spots represent an original and its replicate sample, printed on the array in two-fold dilutions, for each FNA sample. The dilution series represents undiluted, 1:2, 1:4 and 1:8 dilutions of each sample. The baseline phosphorylation level at the time of procurement is represented by the cells directly lysed in lysis buffer (see Table 5, Example V).
Figure 4B:
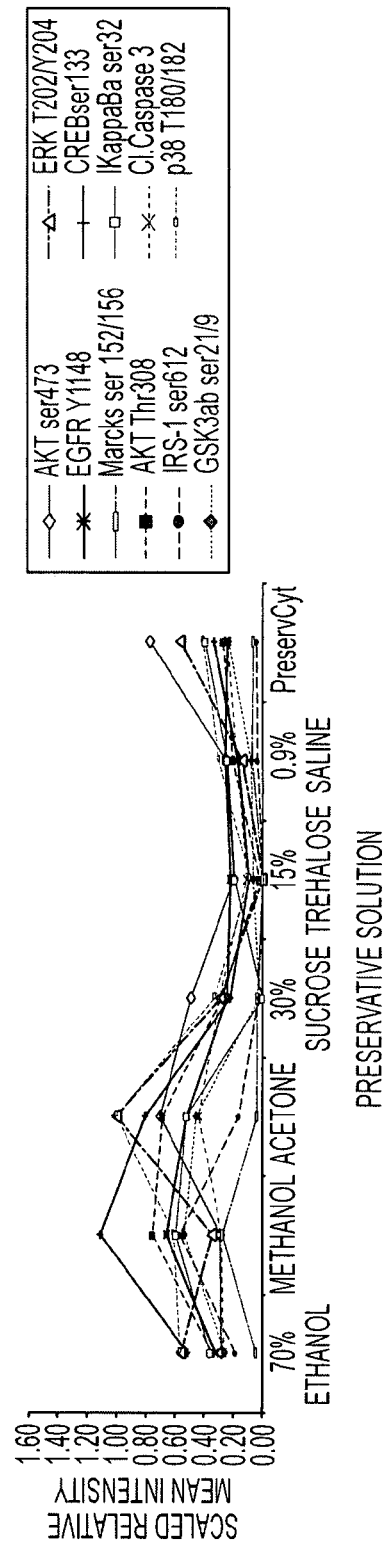
FIG. 4B shows the relative quantity of post-translationally modified proteins from the FNA samples for selected pro-survival and apoptotic endpoints. Direct lysis of the cells preserves the phosphoproteins at the time of procurement. By comparing the samples incubated in different chemical solution to this baseline lysed sample we show that traditional fixatives such as ethanol do not adequately preserve the phosphoproteins. 0.9% saline represents the level of phosphoprotein endpoint deterioration after 24 hours.
Figure 5:
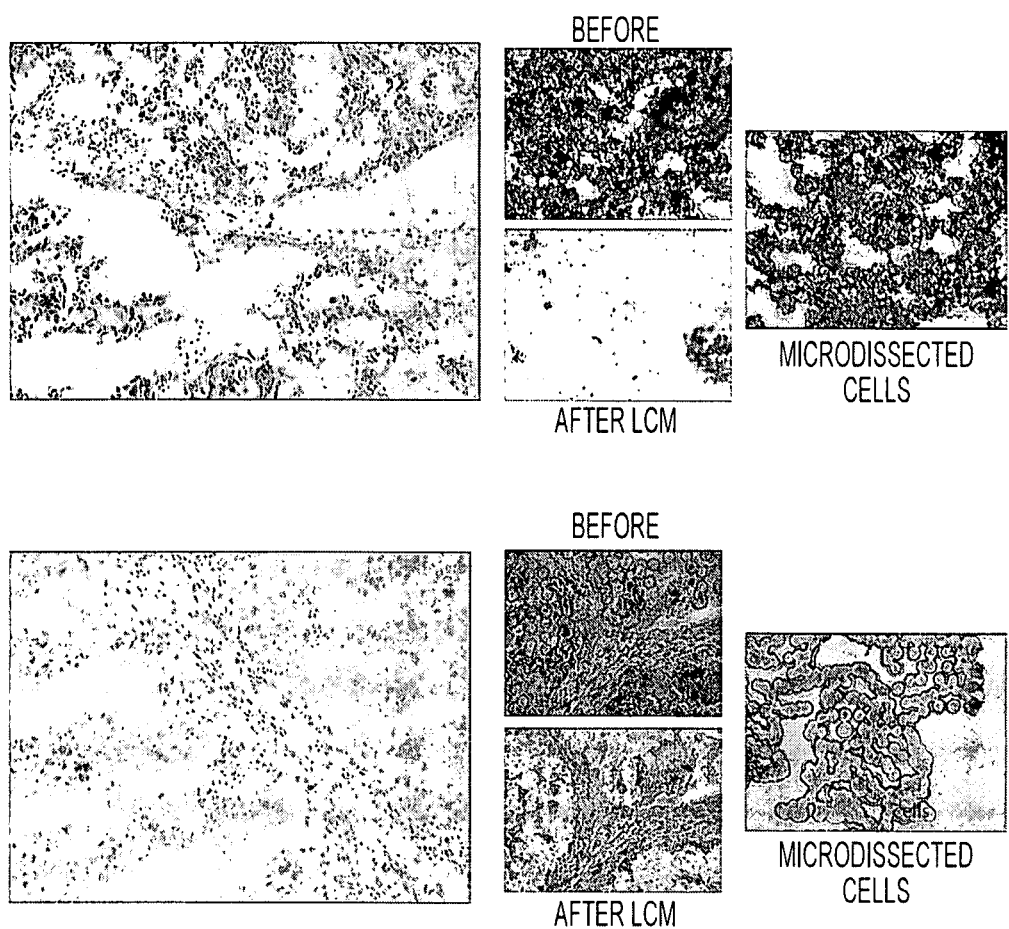
FIG. 5 shows a comparison of tissue morphology between a frozen and fixed tissue sample. Breast tissue metastatic to the brain was either snap frozen or fixed in methanol: water prior to cutting frozen sections. Tissue morphology, the ability to cut frozen sections, and effective laser capture microdissection were comparable in the frozen and methanol:water fixed samples.

Candidate preservative solutions were evaluated that contain combinations of one or more of the following fixatives and/or stabilizers: a) commercial phosphatase inhibitors, b) commercial kinase and proteinase inhibitors, c) 30% sucrose, 15% trehalose stabilizers, d) commercial PreservCyt, e) commercial CytoLyt, f) mild detergent, and g) precipitating fixatives (see Tables 3 and 4 and FIGS. 4 and 5). A suitable combination can be selected, based on this analysis, to generate a preservative candidate is effective for room temperature or 4° C. storage for 24 hours.

TABLE 3

| Chemical | Chemical Formula | Diluent | Additives | Successful cutting frozen tissue section |
|---|---|---|---|---|
| Polyethylene glycol (PEG 400) | $H(OCH_2CH_2)_8OH$ | None | None | No |
| Polyethylene glycol (PEG 400) | $H(OCH_2CH_2)_8OH$ | None | Phosphatase and protease inhibitors | No |
| 30% sucrose | $C_{12}H_{22}O_{11}$ | deionized $H_2O$ | None | Marginal |
| 30% sucrose | $C_{12}H_{22}O_{11}$ | deionized $H_2O$ | Phosphatase and protease inhibitors | Marginal |
| Acetone | $C_3H_6O$ | None | None | No |
| Acetone | $C_3H_6O$ | None | Phosphatase and protease inhibitors | No |
| 70% ethanol | $C_2H_5OH$ | deionized $H_2O$ | None | No |
| 70% ethanol | $C_2H_5OH$ | deionized $H_2O$ | Phosphatase and protease inhibitors | No |
| Cytolyt ® (methanol:water) | $CH_3OH$ | None | None | Yes |
| Cytolyt ® (methanol:water) | $CH_3OH$ | None | Phosphatase and protease inhibitors | Yes with holes |
| 95% ethanol | $C_2H_5OH$ | deionized $H_2O$ | None | No |
| 85% ethanol | $C_2H_5OH$ | deionized $H_2O$ | None | No |
| 75% ethanol | $C_2H_5OH$ | deionized $H_2O$ | None | No |
| 65% ethanol | $C_2H_5OH$ | deionized $H_2O$ | None | No |
| 55% ethanol | $C_2H_5OH$ | deionized $H_2O$ | None | No |
| 45% ethanol | $C_2H_5OH$ | deionized $H_2O$ | None | No |
| 95% methanol | $CH_3OH$ | deionized $H_2O$ | None | No |
| 85% methanol | $CH_3OH$ | deionized $H_2O$ | None | No |
| 75% methanol | $CH_3OH$ | deionized $H_2O$ | None | No |
| 65% methanol | $CH_3OH$ | deionized $H_2O$ | None | No |
| 55% methanol | $CH_3OH$ | deionized $H_2O$ | None | No |
| 45% methanol | $CH_3OH$ | deionized $H_2O$ | None | No |
| 22.5% methanol | $CH_3OH$ | PBS w/o Ca/Mg | 5% Hemolysis buffer | No |
| 22.5% methanol | $CH_3OH$ | PBS w/o Ca/Mg | 1% Hemolysis buffer | No |
| 20% methanol | $CH_3OH$ | deionized $H_2O$ | PEG-NHS | No |
| 20% methanol | $CH_3OH$ | deionized $H_2O$ | 0.5% PEG 8000 (from a 10% w/v stock) | Yes |
| 10% methanol | $CH_3OH$ | deionized $H_2O$ | 0.5% PEG 8000 (from a 10% w/v stock) | Yes |
| 20% methanol | $CH_3OH$ | RPMI 1640 | 0.5% PEG 8000 (from a 10% stock) | Yes |
| 10% methanol | $CH_3OH$ | RPMI 1640 | 0.5% PEG 8000 (from a 10% stock) | Yes |

TABLE 3-continued

| Chemical | Chemical Formula | Diluent | Additives | Successful cutting frozen tissue section |
|---|---|---|---|---|
| 70% ethanol | $C_2H_5OH$ | deionized $H_2O$ | 5% (w/v) Alum | No |
| 70% ethanol | $C_2H_5OH$ | deionized $H_2O$ | 15% (v/v) Lactic acid | No |
| 70% ethanol | $C_2H_5OH$ | deionized $H_2O$ | 30% (v/v) Hydrogen peroxide | No |
| 70% ethanol | $C_2H_5OH$ | deionized $H_2O$ | Phosphate buffered saline (PBS) w/o Ca or Mg | No |

TABLE 4

| Chemical | Chemical Formula | Diluent | Additives |
|---|---|---|---|
| RMPI 1640 media (amino acids, inorganic salts, phenol red, glucose, HEPES, glutathione) | Salts: $Ca(NO_3)_2$—$4H_2O$ $MgSO_4$ KCl $NaHCO_3$ NaCl $Na_2HPO_4$ | None | None |
| Polyethylene glycol (PEG 400) | $H(OCH_2CH_2)_8OH$ | deionized $H_2O$ | None |
| 0.9% w/v saline (sodium chloride) | NaCl | deionized $H_2O$ | None |
| 70% v/v ethanol | $C_2H_5OH$ | deionized $H_2O$ | None |
| 15% w/v Trehalose | $C_{12}H_{22}O_{11}$ | deionized $H_2O$ | None |
| 30% w/v sucrose | $C_{12}H_{22}O_{11}$ | deionized $H_2O$ | None |
| PreservCyt ® (methanol:water) | | None | None |
| Acetone | $C_3H_6O$ | None | None |
| Methanol | $CH_3OH$ | None | None |

Fixative Studies

First Study

Fine Needle Aspirate (FNA) samples were studied in 10 different chemical stabilizers for phosphoproteomic preservation and fixation (see Table 3 for chemical formulations). The results of the liquid tests are shown in FIG. 4: ethanol/methanol precipitating fixatives, comparing various concentrations in water, for their relative preservation of phosphoproteins, compared to each other at 24 hours.

We then tested various solutions for their ability to allow the cutting of frozen sections or microdissection, and to achieve phosphoprotein stability. As shown in FIG. 5, we found that ethanol alone, acetone alone, PEG alone or combinations thereof do not function well in these capacities. However, if a combination of water and low percentage of methanol or ethanol is used (e.g. 10% methanol in water), freezing is not impeded, frozen sections can be cut, and histology is acceptable for LCM (laser capture microdissection) (Table 2). See also FIGS. 11 and 12, for examples of suitable conditions for the preparation of frozen sections.

Figure 6A:
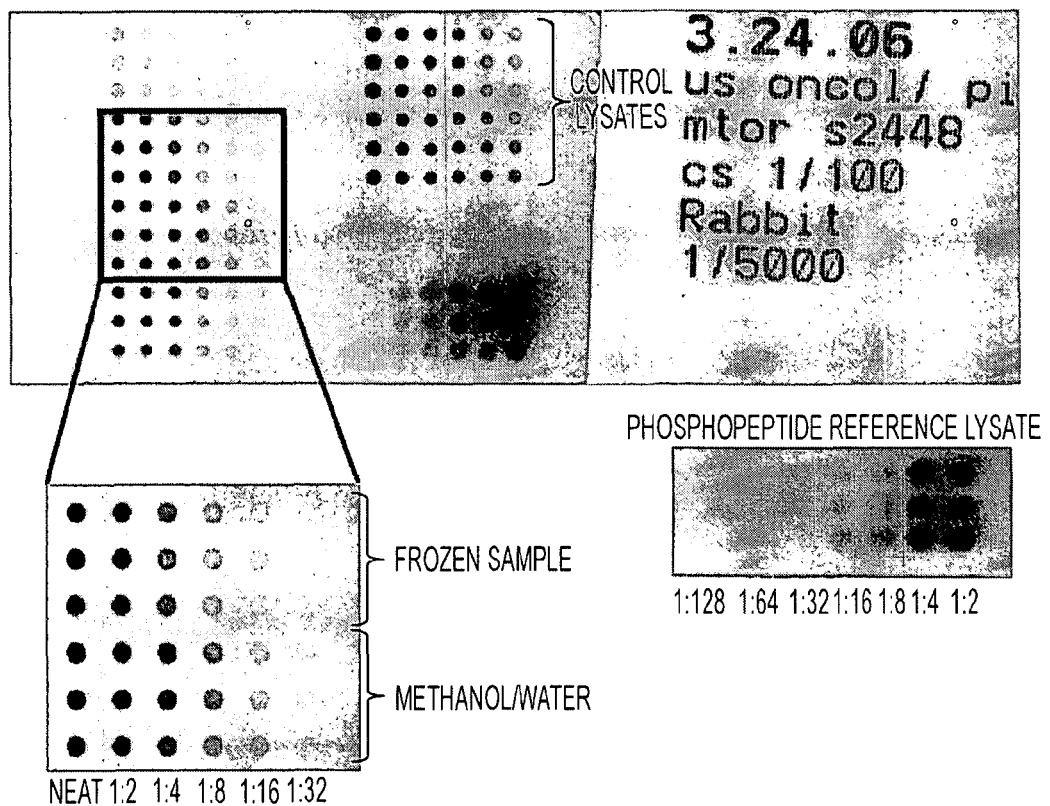
FIG. 6A. Reverse phase protein microarray shows equivalent spot intensities for the fixed and the frozen tissue.
Figure 6B:
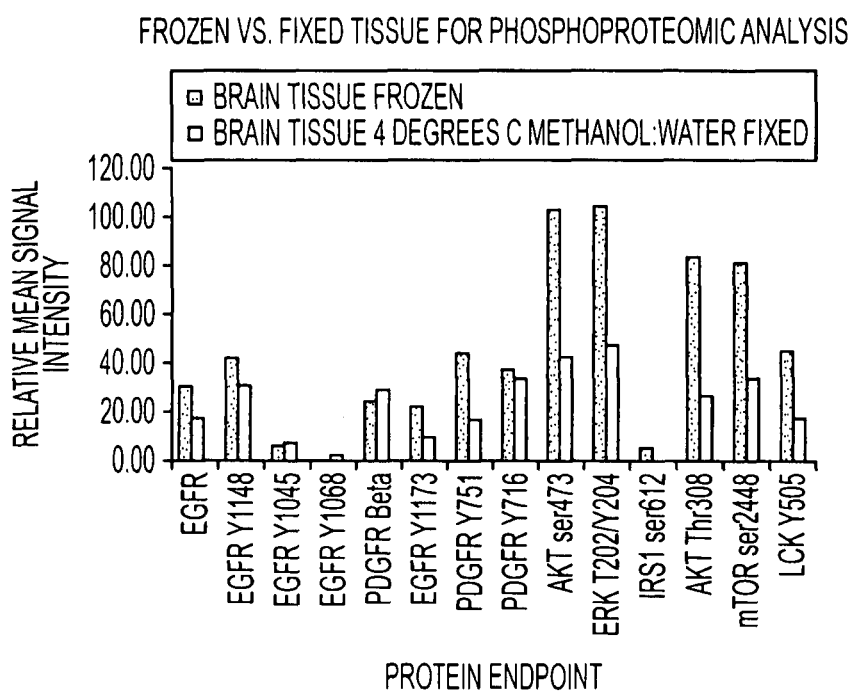
FIG. 6B shows that mean signal intensities are greater in the frozen sample, but the trend between the samples is similar for a variety of protein endpoints.
Figure 7A:
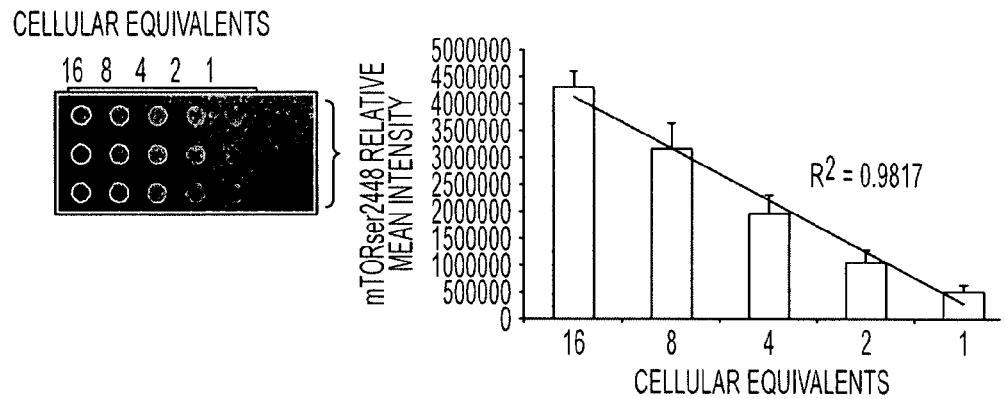
FIG. 7 shows an analysis in which cellular equivalents per sample were printed on reverse phase protein microarrays and the level of mTOR (S2448) phosphorylation was measured. The samples in FIG. 7A were snap frozen. The samples in FIG. 7B were fixed in 20-50% methanol in water. The analyses show equivalence between the sample preservation techniques.
Figure 7B:
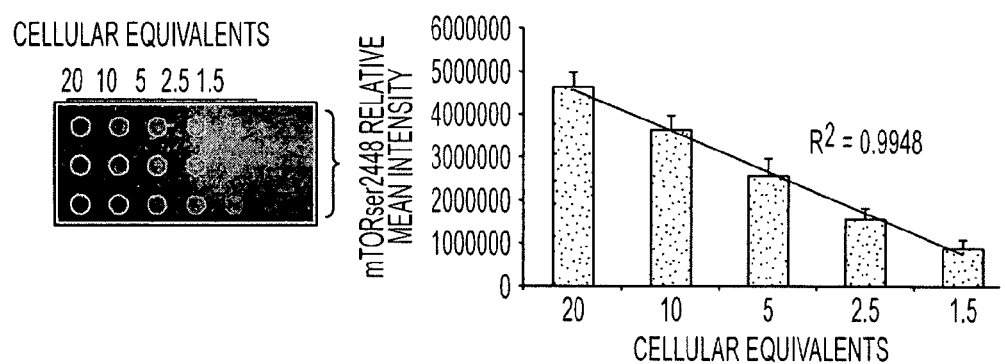

We compared phosphoproteins from real time, room temperature shipping conditions in a methanol:water or ethanol:water fixative to samples that were snap frozen. As shown in FIGS. 6A, 6B and 7, the selected endpoints which were studied showed equivalence of the two methods.

Second Study, to Further Evaluate Phosphoprotein Fixatives

In a further study to identify candidate tissue phosphoprotein stabilizers, various fixative bases were tested with several combinations of inhibitors. The study was carried out essentially as above.

A series of chemistries listed in Tables 2 and 3 were tested for stabilization of phosphoprotein endpoints. Four different stabilizing chemistries were compared for preservation of selected phosphoprotein endpoints. Twenty six end points were evaluated spanning a variety of pathways (Table 1). The four labile phosphoprotein endpoints selected for study—CC3 D175, STAT1 Y701, ASK1 Ser83, EGFR Y1148—were found to fluctuate within the first 30-90 minutes. The data demonstrated that the type of fixative and the additives affect the preservation of the individual tissue analyte, comparing a 15 min post excision value to 24 hours submerged in the candidate preservative. The addition of protease, kinase and phosphatase inhibitors appears to be required for the stabilization of specific endpoints.

Third Study, to Further Evaluate Phosphoprotein Fixatives

Colon tissue was fixed in 85% ethanol, frozen and sectioned. This procedure did not render the tissue suitable for frozen sections, at least because the tissue did not bond to the OCT, thereby leaving a hole in the frozen section. OCT is a standard, art-recognized gel that tissue is placed in to glue it to a chuck for cutting a frozen section. The OCT gel is squirted onto a tissue and the entire block is frozen and then sliced. Preservation in high percentages of other fixatives that act as anti-freezes, such as about 85% methanol, were also found to be unsuitable for freezing. By contrast, tissue (e.g. breast tissue) that was fixed in a preservative containing significantly lower percentages of the fixative (e.g. 40% methanol) and stored at 4° C. for 30 days, then frozen and sectioned, resulted in a smooth frozen section, with no holes. Neither formalin nor paraffin was used during this fixation and slicing procedure.

Fourth Study, to Evaluate Conditions for Preserving Morphology

Figure 12A:
FIG. 12A: Before dissection.
Figure 12B:
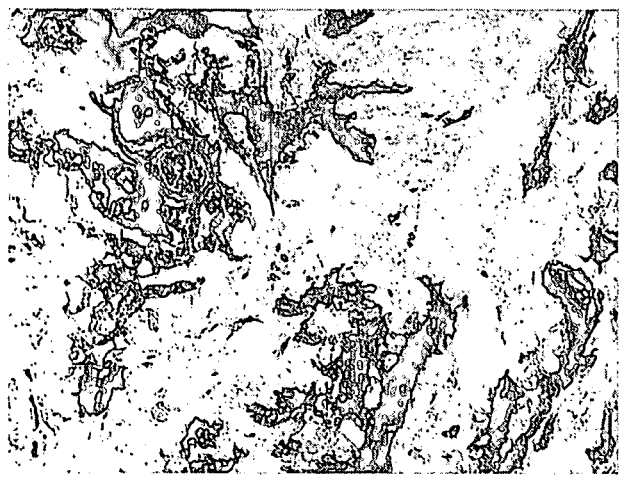
FIG. 12B: after microdissection.
Figure 12C:
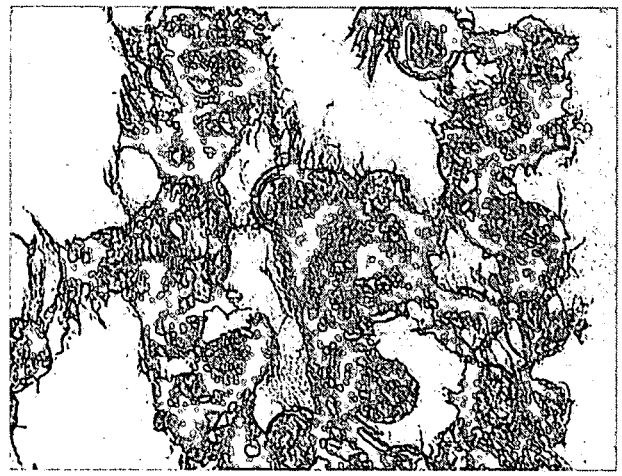
FIG. 12C: procured cells on LCM cap.

The preservation of morphology is important for both diagnosis and microdissection. Morphology preservation of subcellular organelles is a histologic measure of the permeation of a precipitating fixative into the inner mass of the tissue. This example (illustrated in FIGS. 11 and 12) demonstrates the dramatic effect of the addition of the permeation enhancer, PEG, on the morphology of a tissue following 24 hours of tissue incubation in a composition of the invention. For example, the nuclear morphology is well preserved for epithelial glands in the inner tissue mass in the presence of the permeation enhancer, PEG (FIG. 11F), in contrast to the complete lack of preservation of the epithelial cell nuclei in the absence of PEG (FIG. 114D). As shown in FIG. 12, this composition (chemistry) is suitable for laser capture microdissection with an efficiency greater than 95%.

Fifth Study, Showing the Failure of Conventional Fixatives to Stabilize Phosphoproteins A variety of types of tumor tissues were incubated in a series of conventional preservatives to determine if the preservatives were able to stabilize selected phosphoproteins. As shown in Table 5, overall, the tested preservatives were unable to stabilize most of the tested phosphoproteins.

Briefly, tumor tissues from gastrinoma/liver, mesothelioma and parathyroid tumors were sampled by five needle passes and placed into the preservatives listed in Table 5. The samples labeled "Lysis Buffer" were frozen immediately after lysis, and thus represent positive controls in which the phosphoproteins did not undergo any degradation. Immediate lysis and denaturation of the cellular proteins were accomplished by standard Pierce Tissue Protein Extraction Buffer (T-PER), with additional SDS, denaturing reagents, and detergents. The cell samples were stored 24 h in the listed preservatives at 4° C. and then the listed phosphoprotein endpoints were measured. In RPMI medium, the tissue remains alive and wide fluctuations in the phosphoprotein values were noted. Some values dropped to zero while others are markedly elevated compared to the freshly lysed cell baseline. Note in particular that 70% ethanol and PreservCyt, which are standard precipitating fixatives for cellular pathology, resulted in significant, reproducible degradation of the phospho endpoints. They were unable to stabilize the phosphorylation state of key signal proteins over a storage period of 24 hours, which is a typical time delay for cell or tissue shipment. Numbers in the table are relative normalized intensity values using the RPA technology described herein.

TABLE 5

| Sample ID | Normalized data | AKT ser473 | AKT Thr308 | ERK T202/Y204 | GSK3ab ser21/9 | IRS-1 ser612 | EGFR Y1148 | CREBser133 | p38 T180/182 | IKappaBa ser32 | CC3 Asp175 |
|---|---|---|---|---|---|---|---|---|---|---|---|
| Gastrinoma/liver 0.9% saline | 0.9% saline | 3.76 | 9.73 | 10.75 | 12.25 | 4.82 | 39.76 | 24.09 | 33.41 | 29.64 | 14.57 |
| Gastrinoma/liver 15% trehalose | 15% trehalose | 0.00 | 19.93 | 17.01 | 32.18 | 25.51 | 95.78 | 55.11 | 36.95 | 32.99 | 11.19 |
| Gastrinoma/liver 30% sucrose | 30% sucrose | 16.16 | 42.04 | 48.68 | 37.27 | 31.46 | 65.97 | 69.03 | 63.91 | 69.82 | 61.02 |
| Gastrinoma/liver 70% ethanol | 70% ethanol | 0.00 | 0.00 | 11.51 | 19.01 | 19.74 | 39.95 | 103.07 | 27.50 | 28.36 | 5.09 |
| Gastrinoma/liver Acetone | Acetone | 4.56 | 25.45 | 46.15 | 35.47 | 33.10 | 65.10 | 91.79 | 77.58 | 48.91 | 38.23 |
| Gastrinoma/liver Lysis buffer | Lysis Buffer | 13.97 | 38.87 | 37.51 | 29.09 | 34.44 | 65.97 | 79.28 | 66.39 | 67.42 | 33.10 |
| Gastrinoma/liver Methanol | Methanol | 4.15 | 43.73 | 46.47 | 33.59 | 65.97 | 81.50 | 131.23 | 76.09 | 54.98 | 37.64 |
| Gastrinoma/liver PreservCyt | PreservCyt | 5.68 | 10.91 | 22.69 | 23.66 | 3.76 | 26.23 | 34.38 | 35.95 | 25.41 | 17.12 |
| Mesothelioma 0.9% saline | 0.9% saline | 9.78 | 8.97 | 7.72 | 9.46 | 2.34 | 24.62 | 17.20 | 26.34 | 16.87 | 10.85 |
| Mesothelioma 15% trehalose | 15% trehalose | 7.86 | 0.95 | 0.00 | 7.80 | 0.00 | 21.03 | 10.01 | 7.39 | 13.29 | 6.82 |
| Mesothelioma 30% Sucrose | 30% sucrose | 19.36 | 12.13 | 15.67 | 3.12 | 1.84 | 22.84 | 22.82 | 28.71 | 0.00 | 17.90 |
| Mesothelioma 70% ethanol | 70% ethanol | 10.94 | 15.15 | 30.74 | 31.87 | 12.16 | 30.71 | 53.05 | 49.07 | 25.09 | 15.92 |
| Mesothelioma Acetone | Acetone | 27.53 | 30.05 | 55.31 | 55.72 | 10.72 | 49.89 | 83.10 | 87.57 | 36.08 | 26.75 |
| Mesothelioma Methanol | Methanol | 11.14 | 32.75 | 18.87 | 66.02 | 37.33 | 63.00 | 114.37 | 53.36 | 41.23 | 16.93 |
| Mesothelioma RPMI | RPMI | 0.00 | 119.37 | 3.90 | 0.00 | 53.14 | 140.59 | 184.07 | 292.74 | 0.00 | 0.00 |
| Mesotheolima PreservCyt | PreservCyt | 30.51 | 11.93 | 31.11 | 28.89 | 3.05 | 23.03 | 34.82 | 35.68 | 27.46 | 14.62 |
| Parathyroid tumor 0.9% saline | 0.9% saline | 1.84 | 0.00 | 0.00 | 0.00 | 0.00 | 6.57 | 5.35 | 4.79 | 1.87 | 5.46 |
| Parathyroid tumor 15% trehalose | 15% trehalose | 0.26 | 5.38 | 9.34 | 10.36 | 0.05 | 26.55 | 21.50 | 30.53 | 24.12 | 7.76 |
| Parathyroid tumor 30% sucrose | 30% sucrose | 3.27 | 0.00 | 1.15 | 0.00 | 0.00 | 6.14 | 2.09 | 1.15 | 0.33 | 2.23 |
| Parathyroid tumor 70% ethanol | 70% ethanol | 7.18 | 18.57 | 37.27 | 60.83 | 15.92 | 47.58 | 67.91 | 45.63 | 32.97 | 19.16 |
| Parathyroid tumor Acetone | Acetone | 13.12 | 21.93 | 77.97 | 123.00 | 40.55 | 81.36 | 83.74 | 72.96 | 49.65 | 29.46 |
| Parathyroid Lysis buffer | Lysis Buffer | 39.40 | 25.74 | 38.96 | 38.55 | 14.41 | 44.29 | 70.90 | 51.51 | 41.00 | 24.66 |
| Parathyroid Methanol | Methanol | 11.06 | 28.31 | 28.54 | 53.28 | 23.51 | 53.41 | 65.44 | 34.09 | 36.25 | 14.80 |
| Parathyroid RPMI | RPMI | 0.00 | 10.98 | 3.11 | 12.33 | 6.75 | 30.79 | 34.21 | 29.04 | 29.65 | 6.50 |

TABLE 5-continued

| Sample ID | Normalized data | AKT ser473 | AKT Thr308 | ERK T202/Y204 | GSK3ab ser21/9 | IRS-1 ser612 | EGFR Y1148 | CREBser133 | p38 T180/182 | IKappaBa ser32 | CC3 Asp175 |
|---|---|---|---|---|---|---|---|---|---|---|---|
| Parathyroid tumor PreservCyt | PreservCyt | 5.54 | 10.39 | 4.84 | 22.54 | 0.29 | 22.91 | 33.48 | 12.72 | 23.34 | 23.39 |
| Parathyroid tumor Lysis buffer + PI | Lysis Buffer | 7.53 | 0.41 | 1.56 | 4.31 | 0.00 | 8.41 | 6.68 | 4.24 | 8.42 | 6.05 |

Sixth Study, to Show the Effects of Phosphatase Inhibitors or a Kinase Inhibitors Samples from breast tumor and breast adipose tissue were placed in one of three fixative compositions, containing the following stabilizing additives: HBSS (Hank's buffered saline solution) only; HBSS+the phosphatase inhibitors, orthovanadate (100-400 mM) and beta glycerophosphate (375 mM-1.5M); or HBSS+the kinase inhibitors, staurosporine (5.0 uM-20.0 uM) and genistein (0.5 uM-2.0 uM), for 210 minutes at room temperature. Samples were removed at the time points indicated in FIG. 8, and were analyzed by the RPMA procedure as described elsewhere herein for the level of phosphorylation of a variety of phospho-endpoints. including AcCoA(S79), AKT(S473), E-Cadherin, HSP90, IKBa (S32), CC3(Asp175), CC9(Asp330), VEGFR2(Y1175), STAT3(S727), ASK1(S83), MARCKS(S152), ERK(T202/Y204), Beta catenin(S33/S37/T41), IRS-1(S612), SAPK/JNK(Thr183/Tyr185), and Her3(Tyr1289).

The degree of phosphorylation varied widely among the phospho-endpoints tested, reflecting the complex metabolic events (the balance between the addition and removal of phosphate groups from the proteins). In all examples, incubation of the tissue in HBSS alone resulted in decreased levels of post-translationally modified proteins over time (FIG. 8A-D). As an example of hyper-phosphorylation in the presence of phosphatase inhibitors, the presence of phosphatase inhibitors only (HBSS+Phos Inhib) gave rise to increased levels of SAPK/JNK Thr183/Tyr185 and Her3 Tyr1289 over time compared to HBSS only or HBSS+kinase inhibitors (see FIGS. 8A and 8C for SAPK/JNK and Her3, respectively). In the presence of kinase inhibitors only, these same phosphoprotein levels remained relatively stable over time. For other endpoints (e.g., beta catenin(S33/S37/T41)), HBSS+kinase inhibitor stabilized the level of phosphorylation over time compared to either of the other two fixative compositions (FIG. 8B). For others (e.g., CC3(Asp175)), the addition of either a phosphatase or a kinase inhibitor stabilized the cleaved form of the protein compared to HBSS alone (see FIG. 8D). These findings emphasize the desirability of including both a phosphatase and a kinase inhibitor, in a suitable balanced amount, when fixing cells or tissues.

Example IV

Nanoparticle-Based Phosphoproteome Sentinels

Nanoparticles comprising phosphorylated proteins can serve as markers for the preservation state of phosphoproteins in a sample.

In this Example, nanoparticles are incubated with tissues of varying thickness. Permeation of tissues by fluorescently labeled particles is demonstrated by microscopy. If desired, the tissues can be cut into frozen sections and selected cells isolated using laser capture microdissection. The cells (either frozen or at room temperature) are lysed and the contents solubilized. The released particles are then purified from the cellular lysates using magnets. After washing, the purified particles are arrayed on microarrays (e.g. on the same substrate as the protein lysates measured using RPMA). The loss of phosphospecific epitopes from the nanoparticles are compared with changes in phosphoproteomic endpoints in the cellular protein lysates.

Example V

Analysis of the Effect of a Preservative Composition of the Invention on Cell Size and Morphology During Analysis by Flow Cytometry A cell surface receptor glycoprotein, CD4, was selected as a representative protein for evaluation of the effects of the preservative composition on antibody-antigen interactions and cell size and morphology. CD4 is expressed on the surface of T-cells, monocytes, macrophages and dendritic cells and would therefore be present in peripheral blood samples containing white blood cells (WBC).

Peripheral blood was treated with Ficoll density gradient media to provide an enriched source of WBC (bully coat). This buffy coat cell suspension was divided into 4 aliquots for flow cytometry: 1. untreated cells for isotype antibody staining; 2. cells treated with preservative, then stained (10-20% ethanol, 0.5-5% PEG, HBSS with orthovanadate (100-400 mM), beta glycerophosphate (375 mM-1.5M), staurosporine (5.0 uM-20.0 uM), and genistein (0.5 uM-2.0 uM); 3. cells stained first and then treated with fixative; or 4. untreated, no fixative (control).

Figures 13A, 13B:
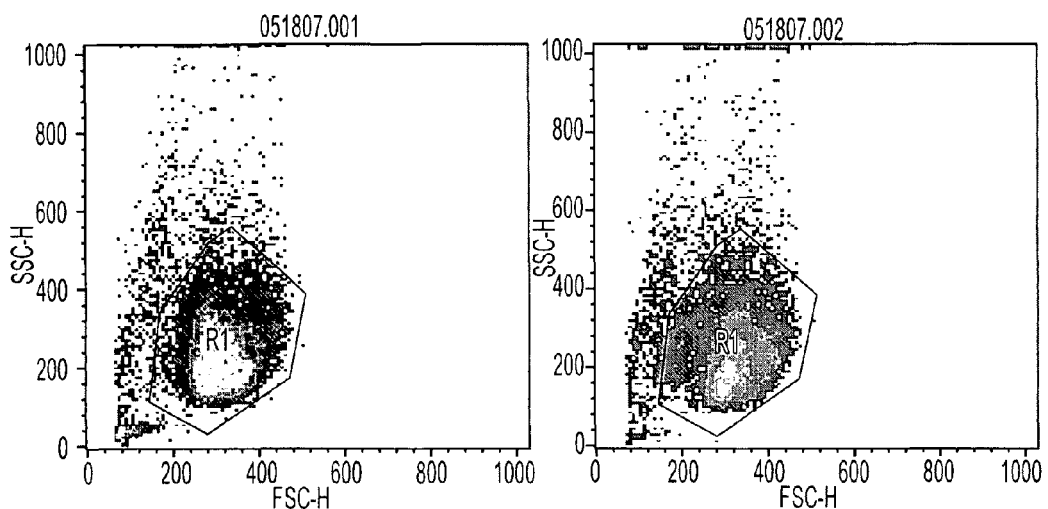
FIG. 13A shows untreated cells stained with an isotype antibody control ($IgG_1$, kappa) FITC conjugated.
FIG. 13B shows cells that were treated for 20 minutes with the preservative composition described in Example V, washed twice and stained with anti-CD4-FITC.
Figures 13C, 13D:
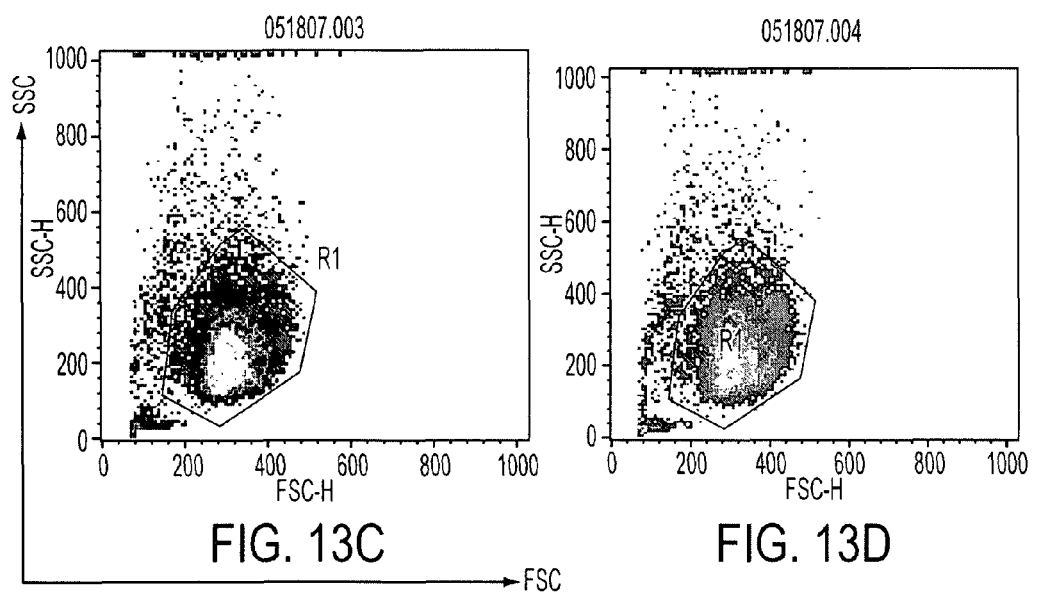
FIG. 13C shows cells that were stained with anti-CD4-FITC initially, washed twice, and then subjected to treatment with the preservative composition.
FIG. 13D shows untreated cells that were stained with anti-CD4-FITC, washed twice and analyzed by flow cytometry (no fixative).

The results of this analysis are presented in FIG. 13. Forward scatter analysis shows consistency in cell size, and side scatter analysis shows consistency in cellular morphology, for cells treated with the fixative composition compared to untreated cells. (A) Untreated cells stained with an isotype antibody control (IgG$_1$, kappa) FITC conjugated. (B) Cells were fixed for 20 minutes with the fixative composition described herein. Cells were then washed twice and stained with anti-CD4-FITC. (C) Cells were stained with anti-CD4-FITC initially, washed twice, and then subjected to fixation with the fixative composition described herein. (D) Untreated cells were stained with anti-CD4-FITC, washed twice and analyzed by flow cytometry (no fixative). Addition of the preservative composition did not significantly affect the size or morphology of the cells, nor did it interfere with antibody staining for Flow Cytometry.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above, including U.S. Provisional Application No. 60/855,120, filed Oct. 30, 2006, and U.S. Provisional Application No. 60/861,086, filed Nov. 27, 2006, and in the figures are hereby incorporated in their entirety by reference.

We claim:

1. A composition for preserving a sample comprising proteins, said composition comprising:
   a. a fixative that stabilizes the proteins in the sample and that has a sufficient water content for a stabilizer and/or a permeability enhancing agent to be soluble therein;
   b. a stabilizer, comprising (i) a kinase inhibitor and (ii) a phosphatase inhibitor, and, optionally, (iii) a protease inhibitor; and
   c. a permeability enhancing agent,
   wherein the proteins are phosphoproteins and wherein the fixative comprises methanol or ethanol, the kinase inhibitor comprises staurosporine or genistein, the phosphatase inhibitor comprises sodium orthovanadate or beta glycerophosphate, and the permeability enhancing agent comprises water, dimethylsulfoxide, or polyethylene glycol.

2. The composition of claim 1, wherein the fixative comprises a particulate material comprising bioceramic, poly diol citrate, chitosan, or hydroxyapatite; a chelation agent; trichloroacetic acid (TCA); chloroform or methanol; or ammonium sulfate.

3. The composition of claim 1, wherein the permeability enhancing agent comprises a polymer or a nanoparticle.

4. The composition of claim 1, further comprising one or more cross-linking agents.

5. The composition of claim 4, wherein the fixative comprises ethanol, the kinase inhibitor comprises staurosporine and genistein, the phosphatase inhibitor comprises sodium orthovanadate and beta glycerophosphate, the permeability enhancing agent comprises polyethylene glycol, and the cross-linking agent comprises dithiobis-succinimidylpropionate.

6. The composition of claim 1, wherein the stabilizer is attached to the permeability enhancing agent.

7. The composition of claim 1, wherein the stabilizer and the permeability enhancing agent are attached to a nanoparticle.

8. A kit for fixing proteins in a sample, comprising the components of the composition of claim 1 and a sentinel comprising a particulate entity attached to one or more surrogate phosphoprotein markers, in one or more containers.

9. A method for preserving proteins in a sample, comprising contacting the sample with the composition of claim 1, under conditions effective for the preservation of proteins in the sample.

10. The method of claim 9, further comprising analyzing the phosphorylation state of at least one phosphoprotein in the sample.

11. The composition of claim 4 wherein the one or more crosslinking agents comprises dithiobis-succinimidylpropionate.

12. A composition for preserving a sample comprising proteins, said composition comprising:
   a. a fixative that stabilizes the proteins in the sample and that has a sufficient water content for a stabilizer and/or a permeability enhancing agent to be soluble therein;
   b. a stabilizer, comprising (i) a kinase inhibitor and (ii) a phosphatase inhibitor;
   c. a permeability enhancing agent; and
   d. a cross-linking agent.

13. The composition of claim 12 wherein the stabilizer further comprises a protease inhibitor.

14. The composition of claim 12 wherein the proteins are phosphoproteins and wherein the fixative comprises methanol or ethanol, the kinase inhibitor comprises staurosporine or genistein, the phosphatase inhibitor comprises sodium orthovanadate or beta glycerophosphate, and the permeability enhancing agent comprises water, dimethylsulfoxide, or polyethylene glycol.

15. The composition of claim 12, wherein the proteins are phosphoproteins and wherein the fixative comprises ethanol, the kinase inhibitor comprises staurosporine and genistein, the phosphatase inhibitor comprises sodium orthovanadate and beta glycerophosphate, the permeability enhancing agent comprises polyethylene glycol, and the cross-linking agent comprises dithiobis-succinimidylpropionate.

16. The composition of claim 13, wherein the proteins are phosphoproteins and wherein the fixative comprises ethanol, the kinase inhibitor comprises staurosporine and genistein, the phosphatase inhibitor comprises sodium orthovanadate and beta glycerophosphate, the permeability enhancing agent comprises polyethylene glycol, and the cross-linking agent comprises dithiobis-succinimidylpropionate.

17. The composition of claim 12, wherein the fixative comprises a particulate material comprising bioceramic, poly diol citrate, chitosan, or hydroxyapatite; a chelation agent; trichloroacetic acid (TCA); chloroform or methanol; or ammonium sulfate.

18. The composition of claim 12, wherein the permeability enhancing agent comprises a polymer or a nanoparticle.

19. The composition of claim 12, wherein the stabilizer is attached to the permeability enhancing agent.

20. The composition of claim 12, wherein the stabilizer and the permeability enhancing agent are attached to a nanoparticle.

21. The composition of claim 14, wherein the fixative comprises about 10-40% ethanol or about 10-40% methanol.

22. The composition of claim 14 wherein
   the phosphatase inhibitor comprises sodium orthovanadate at a concentration of between about 100 mM and about 400 mM or beta glycerophosphate at a concentration of between about 375 mM and 1.5M,
   the kinase inhibitor comprises staurosporine at a concentration of between about 5.0 uM and 20.0 uM or genistein at a concentration of between about 0.5 uM and 2.0 uM, and
   the permeability enhancing agent comprises about 0.5% to about 15% polyethylene glycol.

23. A kit for fixing proteins in a sample, comprising the components of the composition of claim 12 and a sentinel comprising a particulate entity attached to one or more surrogate phosphoprotein markers, in one or more containers.

24. A composition for preserving a sample comprising proteins, said composition consisting essentially of:
   a. a fixative that stabilizes the proteins in the sample and that has a sufficient water content for a stabilizer and/or a permeability enhancing agent to be soluble therein; and
   b. a stabilizer, comprising (i) a kinase inhibitor and (ii) a phosphatase inhibitor;
   c. a permeability enhancing agent; and
   d. a cross-linking agent.

25. The composition of claim 24 further consisting essentially of a protease inhibitor.

26. A method for preserving proteins in a sample, comprising contacting the sample with the composition of claim 12, under conditions effective for the preservation of proteins in the sample.

27. The method of claim 26, further comprising analyzing the phosphorylation state of at least one phosphoprotein in the sample.

28. A method for preserving proteins in a sample, comprising contacting the sample with the composition of claim 24, under conditions effective for the preservation of proteins in the sample.

29. The method of claim 28, further comprising analyzing the phosphorylation state of at least one phosphoprotein in the sample.

* * * * *

UNITED STATES PATENT AND TRADEMARK OFFICE
CERTIFICATE OF CORRECTION

PATENT NO.       : 8,460,859 B2                                     Page 1 of 1
APPLICATION NO.  : 12/447773
DATED            : June 11, 2013
INVENTOR(S)      : Espina et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 633 days.

Signed and Sealed this
Eighth Day of September, 2015

Michelle K. Lee
*Director of the United States Patent and Trademark Office*